United States Patent [19]
Blanc-Ferras et al.

[11] Patent Number: 6,114,336
[45] Date of Patent: Sep. 5, 2000

[54] COSMETIC COMPOSITION CONTAINING A NEUROPEPTIDE Y RECEPTOR ANTAGONIST

[75] Inventors: Elisabeth Blanc-Ferras, Donneville; Françoise Bono Colombie, Toulouse; Bernard Breda, Bougival; Jean Courregelongue, Portet sur Garonne; Catherine Ducasse, Houilles; Remy Mounier, Aulnay-sur-Mauldre; Paul Raymond, Saint Vely Du Fesc; Michel Sabadie, Bernay; Claudine Serradeil-Le-Gal, Escaldens; Vilain Pol, Saussan; Jean-Marie Pereillo, Portet sur Garonne, all of France

[73] Assignee: Sanofi, Paris, France

[21] Appl. No.: 09/119,031

[22] Filed: Jul. 20, 1998

Related U.S. Application Data

[63] Continuation of application No. 08/790,761, Jan. 27, 1997, Pat. No. 5,827,853.

[30] Foreign Application Priority Data

Oct. 23, 1996 [FR] France .................................. 96 12 916

[51] Int. Cl.[7] ..................................................... A01N 43/60
[52] U.S. Cl. .................... 514/255; 252/299.01; 424/450; 424/455; 424/195.1; 428/1; 428/402; 544/337; 544/358
[58] Field of Search ........................ 514/255; 252/299.01; 424/450, 455; 428/1, 402; 544/337, 358

[56] References Cited

U.S. PATENT DOCUMENTS 5,621,079  4/1997  Cascieri et al. .......................... 530/350

FOREIGN PATENT DOCUMENTS

| 0 356 399 A2 | 8/1989 | European Pat. Off. . |
| 35 45 986 A1 | 7/1986 | Germany . |
| 2 138 023 | 10/1984 | United Kingdom . |
| WO 92/00744 | 1/1992 | WIPO . |
| WO 96/14307 | 5/1996 | WIPO . |

OTHER PUBLICATIONS

Castan et al., *Endocrinology*, vol. 131, No. 4, "Identification and Functional Studies of a Specific Peptide YY–Preferring Receptor in Dog Adipocytes", 1972.

Castan et al., *American Physiological Society*, "Distribution of PYY receptors in human fat cells: an antipolytic system alongside the $\alpha_2$ –adrenergic system", E74–80, 1993.

Valet et al., *J. Clin. Invest.*, vol. 85, "Neuropeptide Y and Peptide YY Inhibit Lipolysis in Human and Dog Fat Cells through a Pertussis Toxin–sensitive G Protein", pp. 291–295, Jan. 1990.

Chemical Abstracts, vol. 124, No. 22, (1999).
Chemical Abstracts, vol. 124, No. 6, (1999).

*Primary Examiner*—Terressa M. Boykin
*Attorney, Agent, or Firm*—Jacobson, Price, Holman & Stern, PLLC

[57] ABSTRACT

This invention relates to a cosmetic composition containing at least one NPY-antagonist component mixed with an excipient for cosmetic preparations.

16 Claims, No Drawings

COSMETIC COMPOSITION CONTAINING A NEUROPEPTIDE Y RECEPTOR ANTAGONIST

This is a continuation of application Ser. No. 08/790,761 filed Jan. 27, 1997 now U.S. Pat. No 5,827,853.

The present invention relates to a cosmetic composition containing a neuropeptide Y receptor antagonist. Neuropeptide Y, referred to hereinbelow as "NPY" for short, is a neuromediator which is involved in a certain number of physiological processes and for which an involvement in regulating lipolysis has been demonstrated (P. Valet and M. J. Clin. Invest. 1990, 85, 291–295). NPY receptor antagonists, hereinafter referred to as "NPY antagonists", have been described as medicines, but their efficacy in the treatment of any disease has not been proven to date.

It has now been found that NPY antagonists can be used for the preparation of cosmetic compositions.

More particularly, it has been found that cosmetic compositions containing an NPY-antagonist component can be used as lypolysis/lypogenesis regulators in the skin without, however, interferring with the skin's natural functions.

It has also been found that cosmetic compositions containing an NPY-antagonist component and an α2-antagonist component are particularly advantageous.

Thus, according to one of its aspects, the present invention relates to a cosmetic composition containing at least one NPY-antagonist component mixed with a cosmetic excipient. The NPY antagonist contained in the cosmetic composition may be a non-peptide compound, a peptide, a cell or tissue extract of animal or plant origin or a product obtained by fermentation of a microorganism, for example a bacterium or a fungus.

NPY antagonists which are advantageous in the cosmetic compositions of the present invention are those of groups A, B and C below.

A. Synthetic products selected from groups (I) to (VIII) below are advantageous NPY-antagonist components.

I. Compounds of formula (I)

$$Ar_1-SO_2-N(R_1)-C(CHR'_2)(Ar_2)-C(R_2)(O)-N(H)-CH(R_3N R_4)-CH_2-C_6H_4-C(=N-Q_3)(N-Z_1-Q_1)Q_2 \quad (I)$$

in which $Ar_1$ represents niaphthyl, phenyl, quinolyl or isoquinolyl, optionally substituted with Cl, F, $(C_1-C_4)$alkyl, $(C_1-C_4)$alkoxy, hydroxyl or $(C_1-C_4)$dialkylamino;

$Ar_2$ represents phenyl or thienyl, optionally substituted with Cl, F, $(C_1-C_4)$alkyl, $(C_1-C_4)$alkoxy or hydroxyl;

$R_1$, $R_2$ and $R'_2$ represent, independently of each other, hydrogen, $(C_1-C_4)$alkyl or alternatively $R_1$ represents nothing and N is attached to $Ar_2$ and, optionally, $R_2$ and $R'_2$ form a double bond, or alternatively $R_1$ or $R_2$ is attached to $Ar_2$ and represents $(C_1-C_3)$alkylene;

$R_3$ and $R_4$, which are identical or different, represent hydrogen, $(C_1-C_4)$alkyl or form, with the nitrogen atom to which they are attached, a saturated $C_5-C_7$ heterocycle selected from pyrrolidine, piperidine and hexahydroazepine;

$Z_1$ represents $(C_1-C_{12})$alkylene interrupted or substituted optionally with $(C_5-C_7)$cycloalkyl or phenyl;

$Q_1$ represents methyl, amino, $(C_1-C_4)$alkoxycarbonylamino, $(C_1-C_4)$alkylamino, di$(C_1-C_4)$alkylamino, pyrrolidinyl, piperidino, morpholino, piperazinyl, $(C_1-C_4)$alkyl-4-piperazinyl, amidino, $(C_1-C_4)$alkylamidino, guanidino, $(C_1-C_4)$alkylguanidino, pyridyl, imidazolyl, pyrimidinyl, indolyl, hydroxyl, $(C_1-C_4)$alkoxy, $(C_2-C_8)$alkoxycarbonyl, N-[amino$(C_1-C_4)$alkyl]-N-[$(C_1-C_4)$alkyl] amino, carbamoyl or phenyl optionally substituted with Cl, F, $(C_1-C_4)$alkyl, $(C_1-C_4)$alkoxy or hydroxyl;

$Q_2$ represents hydrogen or $(C_1-C_4)$alkyl;

$Q_3$ represents hydrogen or $(C_1-C_4)$alkyl or $Q_1$ and $Q_3$ are linked to form a heterocycle and together represent $(C_2-C_3)$alkylene whereas $Z_1$ represents nothing, in the form of pure enantiomers or mixtures thereof in any proportions, as well as the addition salts thereof with acids; which can be prepared according to EP 614,911.

II—Raloxifen analogues, in particular a) Compounds of formula (II)

$$ \text{(II)} $$

[Structure: benzothiophene/indole-type core with substituents $R°$, $A°$, $R°_1$, and $-O-CH_2CH_2-X°-R°_2$]

in which:

$A°$ is $-O-$, $-S(O)_m-$, $-N(R°_6)-$, $-(CH_2)_2-$ or $-CH=CH-$;

$R°_6$ is hydrogen or a $(C_1-C_6)$alkyl, and m is 0, 1 or 2;

$X°$ is a bond or a $(C_1-C_4)$alkenylene;

$R°_2$ is a group of formula $$-N(R°_4)(R°_5)$$

in which $R°_4$ and $R°_5$ are, independently, a $(C_1-C_6)$alkyl or constitute, with the nitrogen atom to which they are attached, a heterocyclic group selected from hexamethyleneiminyl, piperazino, heptamethyleneiminyl, 4-methylpiperidyl, imidazolinyl, piperidyl, pyrrolidinyl or morpholinyl;

$R°$ is a hydroxyl, a halogen, a hydrogen, a $(C_3-C_8)$cycloalkyl, a $(C_2-C_7)$alkanoyloxy, a $(C_1-C_6)$alkoxy or a phenyl, the said phenyl optionally being substituted with one, two or three substitutents selected from groups consisting of $(C_1-C_4)$alkyl, $(C_1-C_4)$alkoxy, nitro, chloro, fluoro, trifluoromethyl, $-OSO_2-(C_1-C_{10})$alkyl or $-O-C(O)-NH-R°_3$;

$R_1$ is hydroxyl, halogen, hydrogen, $(C_3-C_8)$cycloalkyl, $(C_2-C_7)$alkanoyloxy, $(C_1-C_6)$alkoxy or phenyl, it being possible for the said phenyl optionally to be substituted with one, two or three substituents selected from the group consisting of $(C_1-C_4)$alkyl, $(C_1-C_4)$alkoxy, nitro, chloro, fluoro, trifluoromethyl, $-OSO_2-(C_1-C_{10})$alkyl or $-O-C(O)-N-R°_3$;

in which each $R°_3$ represents, independently, $(C_1-C_6)$alkyl, $(C_3-C_8)$cycloalkyl, unsubstituted or substituted phenyl in which the substitutent is halogen, $(C_1-C_6)$alkyl or $(C_1-C_6)$alkoxy; with the limitation that when $X°$ is a bond and $A°$ is $-S-$, then $R°$ and $R°_1$ are not both selected from the group consisting of hydroxyl, methoxy and (C₂–C₇)alkanoyloxy; as well as the salts or solvates thereof, which can be prepared according to WO 96/12489, in particular a compound selected from:

3-(4-methoxyphenyl)-4-[4-(2-pyrrolidin-1-ylethoxy) benzoyl]1,2-dihydronaphthalene, 3-phenyl-4-[4-(2-pyrrolidin-1-ylethoxy)benzoyl]-7-methoxy-1,2-dihydronaphthalene, 3-(4-methoxyphenyl)-4-[4-[2-(piperid-1-yl)ethoxy]benzoyl]-1,2-dihydronaphthalene, 3-(4-hydroxyphenyl)-4-[4-[2-(pyrrolidin-1-yl)ethoxyl-benzoyl]-1,2-dihydronaphthalene, 3-(4-methoxyphenyl)-4-[4-[2-(hexamethyleneimin-1-yl) ethoxy]benzoyl]-1,2-dihydronaphthalene, 3-(4-methoxyphenyl)-4-[4-[2-(piperid-1-yl)ethoxy]benzoyl]-1,2-dihydronaphthalene, 3-(4-methoxyphenyl)-4-[4-[2-(piperid-1-yl)ethoxy]benzoyl]-7-methoxy-1,2-dihydronaphthalene, 3-(4-methoxyphenyl)-4-[4-[2-(N-methyl-1-pyrrolidinium) ethoxy]benzoyl]-1,2-dihydronaphthalene, 3-(4-methoxyphenyl)-4-[4-(2-dimethylaminoethoxy)benzoyl]-1,2-dihydronaphthalene, 3-(4-methoxyphenyl)-4-(4-diethylaminoethoxybenzoyl)-1, 2-dihydronaphthalene, 3-(4-methoxyphenyl)-4-(4-diisopropylaminoethoxybenzoyl)-1,2-dihydronaphthalene, 2-(4-hydroxyphenyl)-3-[4-[2-(hexamethyleneimin-1-yl) ethoxy]benzoyl]-6-hydroxybenzofuran, 2-(4-hydroxyphenyl)-3-[4-[2-(piperid-1-yl)ethoxy] benzoyl]-6-hydroxybenzofuran, 2-(4-hydroxyphenyl)-3-[4-[2-pyrrolidin-1-yl)ethoxy] benzoyl]-6-hydroxybenzofuran, 2-(4-hydroxyphenyl)-3-[4-[2-(N,N-diethylamino)ethoxy] benzoyl]-6-hydroxybenzofuran, 2-(4-hydroxyphenyl)-3-[4-[2-(N,N-diisopropylamino) ethoxy]benzoyl]-6-hydroxybenzofuran, 2-(4-hydroxyphenyl)-3-[4-[2-(N,N-dimethylamino)ethoxy] benzoyl]-6-hydroxybenzofuran, 1-ethyl-2-(4-methoxyphenyl)-3-[4-[2-(piperid-1-yl)ethoxy] benzoyl]-6-hydroxyindole, 2-(4-methoxyphenyl)-3-[4-[2-(hexamethyleneimin-1-yl) ethoxy]benzoyl]-6-methoxybenzofuran, 2-(4-methoxyphenyl)-3-[4-[2-(piperid-1-yl)ethoxy] benzoyl]-6-methoxybenzofuran, 2-(4-methoxyphenyl)-3-[4-[2-(pyrrolidin-1-yl)ethoxy] benzoyl]-6-methoxybenzofuran, 2-(4-methoxyphenyl)-3-[4-[2-(N,N-diethylamino)ethoxy] benzoyl]-6-methoxybenzofuran, 2-(4-methoxyphenyl)-3-[4-[2-(N,N-diisopropylamino) ethoxy]benzoyl]-6-methoxybenzofuran, 2-(4-methoxyphenyl)-3-[4-[2-(N,N-dimethylamino)ethoxy) benzoyl]-6-methoxybenzofuran, 1-ethyl-2-(4-methoxyphenyl)-3-[4-[2-(piperid-1-yl)ethoxy] benzoyl]-6-methoxyindole, 2-(4-methoxyphenyl)-3-[4-[3-(hexamethyleneimin-1-yl) propoxy]benzoyl]benzo[b]thiophene, 2-(4-methoxyphenyl)-3-[4-[2-(hexamethyleneimin-1-yl) ethoxy]benzoyl]benzo[b]thiophene, 2-(4-methoxyphenyl)-3-[4-[3-(piperid-1-yl)propoxy] benzoyl]benzo[b]thiophene, 2-(4-methoxyphenyl)-3-[4-[2-(pyrrolidin-1-yl)ethoxy] benzoyl]benzo[b]thiophene, 2-(4-methoxyphenyl)-3-[4-[2-(N,N-diethylamino)ethoxy] benzoyl]benzo[b]thiophene, 2-(4-methoxyphenyl)-3-[4-[2-(N,N-diisopropylamino) ethoxy]benzoyl]benzo[b]thiophene, 2-(4-methoxyphenyl)-3-[4-[2-(N,N-dimethylamino)ethoxy] benzoyl]benzo[b]thiophene, 2-(4-chlorophenyl)-3-[4-[2-(hexamethyleneimin-1-yl) ethoxy]benzoyl]-6-hydroxybenzo[b]thiophene, 2-(4-hydroxyphenyl)-3-[4-[2-(piperid-1-yl)ethoxy]benzoyl]benzo[b]thiophene, 2-(4-hydroxyphenyl)-3-[4-[2-(pyrrolidin-1-yl)ethoxy] benzoyl]benzo[b]thiophene, 2-(4-hydroxyphenyl)-3-[4-[2-(N,N-diethylamino)ethoxy] benzoyl]benzo[b]thiophene, 2-(4-hydroxyphenyl)-3-[4-[2-(N,N-diisopropylamino) ethoxy]benzoyl]benzo[b]thiophene, 2-(4-hydroxyphenyl)-3-[4-[2-(N,N-dimethylamino)ethoxy] benzoyl]benzo[b]thiophene, 2-(4-chlorophenyl)-3-[4-[2-(pyrrolidin-1-yl)ethoxy]benzoyl]benzo[b]thiophene 1-oxide, 2-(4-chlorophenyl)-3-[4-[2-(piperid-1-yl)ethoxy]benzo-yl] benzo[b]thiophene 1-oxide,

[6-(n-butylsulphonyl)-2-[4-(n-butylsulphonyl)phenyl]benzo [b]thien-3-yl][4-[2-(1-piperidyl)ethoxy]phenyl-methanone,

[6-(n-pentylsulphonyl)-2-[4-(n-pentylsulphonyl)phenyl] benzo[b]thien-3-yl][4-[2-(1-piperidyl)ethoxy]phenyl] methanone,

[6-(n-hexylsulphonyl)-2-[4-(n-hexylsulphonyl)phenyl] benzo[b]thien-3-yl][4-[2-(1-piperidyl)ethoxy]phenyl] methanone,

[6-(n-butylsulphonyl)-2-[4-(n-butylsulphonyl)phenyl]benzo [b]thien-3-yl][4-[3-(1-piperidyl)propyloxy]phenyl] methanone,

[6-(n-butylsulphonyl)-2-[4-(n-butylsulphonyl)phenyl]benzo [b]thien-3-yl]-[4-[2-(1-pyrrolidinyl)ethoxy]phenyl] methanone,

[6-hydroxy-2-[4-(n-butylsulphonyl)phenyl]benzo[b]thien-3-yl]-[4-[2-(1-piperidyl)ethoxylphenyl]methanone,

[6-n-butylsulphonyl-2-[4-hydroxyphenyl]benzo[b]thien-3-yl]-[4-[2-(1-piperidyl)ethoxy]phenyl]methanone,

[6-[N-(4-chlorophenyl)carbamoyl]-2-[4-[N-(4-chlorophen-yl)carbamoyl]phenyl]benzo[b]thien-3-yl][4-[2-(1-piperidyl)ethoxy]phenyl]methanone,

[6-(N-(n-butyl)carbamoyl]-2-[4-[N-(n-butyl)carbamoyl] phenyl]benzo[b]thien-3-yl][4-[2-(1-piperid-yl)ethoxy] phenyl]methanone,

[6-(N-methylcarbamoyl)-2-[4-(N-methylcarbamoyl)phenyl] benzo[b]thien-3-yl][4-[2-(1-piperidyl)ethoxy]phenyl] methanone,

[6-(N-ethylcarbamoyl)-2-[4-(N-ethylcarbamoyl)phenyl] benzo[b]thien-3-yl][4-[2-(1-piperidyl)ethoxylphenyl] methanone, (6-(N-isopropylcarbamoyl)-2-[4-(N-isopropylcarbamoyl) phenyl]benzo[b]thien-3-yl][4-[2-(1-piperidyl)ethoxy] phenyl]methanone,

[6-(N-cyclohexylcarbamoyl)-2-[4-(N-cyclohexylcarbamo-yl)phenyl]benzo[b]thienyl-3-yl][4-[2-(1-piperidinyl) ethoxy]phenyl]methanone and the salts and solvates thereof.

(b) Compounds of formula (III)

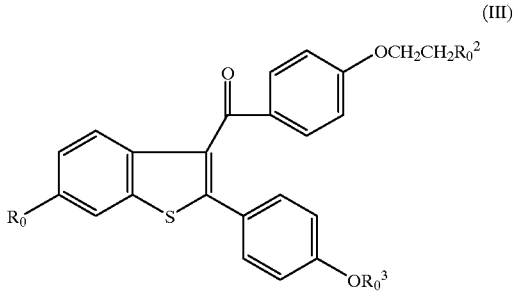

in which $R_0$ and $R^3{}_0$ represent, independently, H, CH$_3$, —CO— (C$_1$–C$_6$)alkyl or optionally substituted phenyl and $R^2{}_0$ represents pyrrolidino, piperidino, hexamethyleneimino or the pharmaceutically acceptable salts or solvates thereof, NPY antagonists described in U.S. Pat. No. 5,504,094, in particular the compound of formula (III) in which $R_0$ and $R^3{}_0$ are both hydrogen and $R^2{}_0$ is pyrrolidino, as well as the salts and solvates thereof.

III—Phenylsulphonylquinolines of formula (IV):

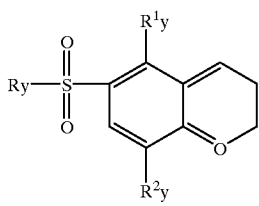

in which Ry is an optionally substituted aryl, or $R^1y$ is —NO$_2$, —CH, —CO$_2R^3y$ in which $R^3y$ is H, alkyl or aryl, —SO$_2R^3y$ in which $R^3y$ is as defined above, or

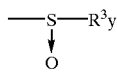

in which $R^3y$ is as defined above, or

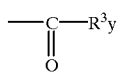

in which $R^3y$ is as defined above, $R^2y$ is —HN$_2$, —OH or —SH and salts thereof, described in U.S. Pat. No. 5,552,411, in particular 8-amino-6-(2-isopropylphenylsulphonyl)-5-nitroquinoline known under the code PD-160170 and 8-amino-6-(4-aminophenylsulphonyl)-5-nitroquinoline, known under the code PD-9262, which are described in Bioorganic and Medicinal Chemistry Letters, 1996, 6, 15, 1809–1814.

IV—Benextramine and analogues thereof described in J. Med. Chem. 1993, 36, 272–279, in Eur.

J. Pharmacology 1994, 37, 2242–2248 and in Current Pharmaceutical Design, 1995, I, 295–304, in particular SC3117, SC3199, CC217 and CC2137.

V—Inositol phosphate derivatives, in particular:

a) specific isomers of inositol triphosphate, in particular D-myoinositol 1,2,6-triphosphate, myoinositol 1,2,3-triphosphate and L-myoinositol 1,3,4-triphosphate, which are described as NPY antagonists in WO 92/00079 and U.S. Pat No. 5,128,332.

b) Inositol monophosphate in acidic form and salts thereof, in particular the sodium, potassium, calcium or zinc salts, which are described as NPY antagonists in WO 92/00744.

VI—Compounds of formula

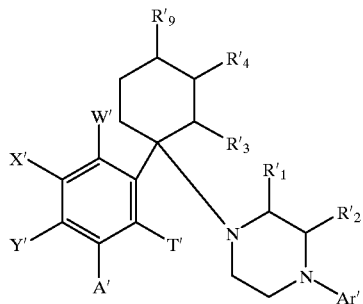

in which:

Ar' is phenyl, 2-, 3- or 4-pyridyl, 2- or 3-thienyl, 4 or 5-pyrimidinyl, each optionally being mono- or disubstituted with a halogen, a hydroxyl or a linear or branched lower alkyl chain having from 1 to 6 carbon atoms;

A', W', X', Y' and T' are identical or different and represent a hydrogen, a halogen, a hydroxyl, a linear or branched lower alkoxy chain having 1 to 6 carbon atoms;

$R'_1$ and $R'_2$ are identical or different and represent a hydrogen, a linear or branched lower alkyl chain having 1 to 6 carbon atoms;

$R'_3$ and $R'_4$ are identical or different and represent a hydrogen or a linear or branched lower alkyl chain having 1 to 6 carbon atoms; and $R'_9$ represents a hydrogen, a linear or branched lower alkyl chain having 1 to 6 carbon atoms or a phenyl;

and salts thereof, which can be prepared as described in WO 96/14307, in particular 1-cyano-1-(4-phenylpiperazin-1-yl)cyclohexane, 1-phenyl-1-(4-phenylpiperazin-1-yl)cyclohexane, 1-(3-methoxyphenyl)-1-(4-phenylpiperazin-1-yl) cyclohexane, 1-(3-methoxyphenyl)-1-[4-(2-pyrimidinyl)piperazin-1-yl] cyclohexane, 1-(3-methoxyphenyl)-1-[4-(2-pyridyl)piperazin-1-yl] cyclohexane, 1-(3-methoxyphenyl)-1-[4-(2-fluorophenyl)piperazin-1-yl] cyclohexane, 1-(3-methoxyphenyl)-1-[4-(4-fluorophenyl)piperazin-1-yl] cyclohexane, 1-(3-hydroxyphenyl)-1-(4-phenylpiperazin-1-yl) cyclohexane, 1-(3,5-dimethoxyphenyl)-1-(4-phenylpiperazin-1-yl) cyclohexane, 1-(3-ethoxyphenyl)-1-(4-phenylpiperazin-1-yl) cyclohexane, 1-(3-methoxyphenyl)-1-(4-phenylpiperazin-1-yl)-4-phenylcyclohexane, 1-(3-n-butoxyphenyl)-1-(4-phenylpiperazin-1-yl) cyclohexane, 1-(3-methoxyphenyl)-1-(4-phenylpiperazin-1-yl)-4-methylcyclohexane dihydrochloride cis isomer and trans isomer, 1-(4-methoxyphenyl)-1-(4-phenylpiperazin-1-yl) cyclohexane, 1-(2-methoxyphenyl)-1-(4-phenylpiperazin-1-yl)
cyclohexane,
1-(3,4-methylenedioxyphenyl)-1-(4-phenylpiperazin-1-yl)
cyclohexane,
1-(3-ethoxyphenyl)-1-(4-phenylpiperazin-1-yl)-4-methyl-
cyclohexane cis isomer and trans isomer,
1-(3-ethoxyphenyl)-1-(4-phenylpiperazin-1-yl)-4-ethyl-
cyclohexane cis isomer and trans isomer,
1-(3-isopropoxyphenyl)-1-(4-phenylpiperazin-1-yl)-4-
methylcyclohexane cis isomer and trans isomer,
1-(3-methoxyphenyl)-1-(4-phenylpiperazin-1-yl)-3-
methylcyclohexane cis isomer and trans isomer,
1-(3-benzyloxyphenyl)-1-(4-phenylpiperazin-1-yl)
cyclohexane,
4-(3-ethoxyphenyl)-4-(4-phenylpiperazin-1-yl)tetra-
hydropyran,
4-(3-ethoxyphenyl)-4-(4-phenylpiperazin-1-yl)tetra-
hydrothiopyran,
1-(3-methoxymethoxyphenyl)-1-(4-phenylpiperazin-1-yl)-
4-methylcyclohexane cis isomer and trans isomer,
1-(3-ethoxymethoxyphenyl)-1-(4-phenylpiperazin-1-yl)-4-
methylcyclohexane cis isomer and trans isomer,
1-(3-ethoxyphenyl)-1-(4-phenylpiperazin-1-yl)-4-
methoxycyclohexane cis isomer and trans isomer.

VII—Compounds of formula

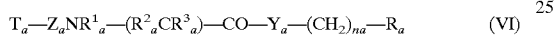

(VI)

in which
$n_a$ represents 0, 1, 2, 3, 4 or 5;
$R_a$ represents a hydrogen atom or a phenyl or naphthyl group
optionally mono- or disubstituted with identical or different substituents selected from a fluorine, chlorine, bromine or iodine atom, a cyano, alkyl, phenyl, hydroxyl, alkoxy, dialkylaminoalkoxy, hydroxyphenyl, phenylalkoxy, alkylcarbonyl, amino, alkylamino, dialkylamino, alkylsulphonylamino, alkylcarbonylamino, alkoxycarbonylamino, alkoxycarbonyloxy, carboxyl, alkoxycarbonyl, aminocarbonyl, alkylaminocarbonyl, dialkylaminocarbonyl, alkylcarbonyloxy, alkylsulphonyloxy, hydroxymethyl, hydroxyethyl, hydroxypropyl, hydroxybutyl, trifluoromethyl, trifluoromethoxy, trifluoromethylthio, aminoalkyl, alkylaminoalkyl, aminocarbonylaminoalkyl, benzoylamino, alkanoylaminoalkyl, alkoxycarbonylaminoalkyl, benzyloxycarbonylaminoalkyl, aminosulphonyl, alkylaminosulphonyl, dialkylaminosulphonyl, aminosulphonylamino, alkylaminosulphonylamino, dialkylaminosulphonylamino, cyanamino, aminocarbonylamino, alkylaminocarbonylamino, dialkylaminocarbonylamino, aminosulphonylaminoalkyl, alkylaminosulphonylaminoalkyl, carboxyalkyl, alkoxycarbonylalkyl, aminocarbonylalkyl, alkylaminocarbonylalkyl, aminosulphonylalkyl, alkylaminosulphonylalkyl, alkylsulphonyl, aminosulphonyloxy, alkylaminosulphonyloxy, dialkylaminosulphonyloxy or cyanoguanidino group,
an aminophenyl or aminonaphthyl group disubstituted with a chlorine or bromine atom, wherein the substituents may be identical or different, or
a hydroxyphenyl or hydroxynaphthyl group disubstituted with a chlorine or bromine atom or with alkyl or alkoxy groups, wherein the substituents may be identical or different,
a diphenylmethyl group, an aminocarbonylalkyl group substituted on the alkyl part with a hydroxyphenylalkyl group or with a (2,2-diphenylethyl)aminocarbonylaminophenyl group,
a 5-membered heteroaryl group attached via a carbon or nitrogen atom, the said heteroaryl comprising an imino group optionally substituted with a ($C_1$–$C_6$)alkyl group or a phenyl group and an oxygen, sulphur or nitrogen atom, or a 6-membered heteroaryl group attached via a carbon atom, the said heteroaryl comprising one or two nitrogen atoms,
as well as the 5- or 6-membered heteroaromatic rings defined above which constitute a heteroaromatic bicyclic system with two neighbouring carbon atoms of the heteroaromatic ring and a 1,4-butadienylene group, and, furthermore, all the mono- or bicyclic heteroaryl groups mentioned above may be monosubstituted on the carbon skeleton with a fluorine, chlorine or bomine atom, with an alkyl, alkoxy, hydroxyl, phenyl, nitro, cyano, carbonyl, alkoxycarbonyl, aminocarbonyl, alkylaminocarbonyl, dialkylaminocarbonyl, fluoromethyl, difluoromethyl, trifluoromethyl, alkanoyl, aminosulphonyl, alkylaminosulphonyl or dialkylaminosulphonyl group, or disubstituted with a fluorine, bromine or chlorine atom, with methyl, methoxy or hydroxyl groups, wherein the substituents may be identical or different,
a phenyl group substituted with a (1,5-dihydro-2,4(3H) dioxoimidazol-3-yl)alkyl or with a [1,2-dihydro-3,5(4H) dioxo-3H-1,2,4-triazol-4-yl]alkyl residue, in which the imidazole or triazole part is substituted with 1 or 2 phenyl groups,
a cycloalkyl group having from 4 to 8 carbon atoms optionally substituted with a hydroxyl, amino, alkylamino or dialkylamino group, wherein te substituents described above are not attached to position 1 of the cycloalkyl residue when Y represents an oxygen atom,
a 1-[[[5,11-dihydro-6(6H)oxopyrido[2,3-b][1,4] benzodiazepin-11-yl]carbonyl]methyl]-4-piperidyl group or a 3-hydroxy-1-propin-1-yl group, a 2,3-dihydro-1H-isoindol-2-yl group optionally substituted on the nitrogen atom with a diphenylaminocarbonyl group, or a hydroxyl group, when $Y_a$ is an oxygen atom or a group
—$NR^4{}_a$— and $n_a$ represents a figure between 2 and 5,
$R_3$ is a hydrogen atom, a linear or branched ($C_1$–$C_{10}$)alkyl group, a cycloalkyl group having from 3 to 7 carbon atoms, a phenyl group optionally substituted with a hydroxyl or hydroxyalkyl group, or a phenylmethyl group optionally substituted on the phenyl part with a hydroxyl or hydroxyalkyl group,
$R^2{}_3$ is an unbranched ($C_1$–$C_5$) alkyl substituted in the ω position with an amino or alkylamino group which is protected by an amine-protecting group, with a dialkylamino, N-alkylbenzylamino, aminocarbonyl, aminocarbonylamino, aminoethylimine, aminoiminomethyl, amino (hydroxyimino)methyl, amino (alkoxyimino) methyl, guanidino, hydrazinoiminomethyl, amino (nitroimino) methyl, [amino (nitroimino)methyl] amino, amino (cyanimino)methyl, [amino(cyanimino) methyl]amino, [(alkylamino) iminomethyl]amino, [(alkylamino) (alkylimino)methyl]amino, [amino (alkylimino)methyl]amino, 2-aminoimidazol-1-yl, (5-amino-4H-1,2,4-triazol-3-yl)amino, (5-amino-4H-1,2, 4-triazol-3-yl)methylamino, (3-amino-1,2,4-oxadiazol-5-yl)amino or (5-amino-1,2,4-oxadiazol-3-yl)amino group or with an imidazol-4-yl, imidazol-2-yl, 1-methylimidazol-2-yl, imidazol-2-ylamino, imidazol-2-ylmethylamino or (4,5-dihydro-1H-imidazol-2-yl)amino group, optionally substituted on the carbon with one or two methyl groups, or a phenyl or phenylmethyl group optionally substituted on the aromatic rings with a cyano, iminomethylamino, cyaniminomethylamino, (methylamino)methylideneamino, aminoiminomethyl, amino (hydroxyimino)methyl, amino(alkoxyimino)methyl, hydrazinoiminomethyl, amino(cyanimino)methyl or guanidino group or with an imidazol-2-yl, 1-methylimidazol-2-yl or 4,5-dihydro-1H-imidazol-2-yl group, optionally substituted on the carbon atoms with one or two methyl groups, in which, in the aminoiminomethyl, amino(hydroxyimino)methyl and guanidino groups mentioned in the definition of $R^2_a$ above, one or more hydrogen. atoms connected to the nitrogen atom, independent of each other, may be replaced by alkyl groups, or in which two hydrogen atoms connected to different nitrogen atoms may be replaced by an alkyl bridge having from 2 to 4 carbon atoms and for which the hydrogen atom of an HN<, HN= or $H_2N$ group in the residue $R^2_a$ may be substituted with an alkoxy carbonyl group having from 2 to 7 carbon atoms, with a phenylalkoxycarbonyl group in which the alkyl is $C_1–C_6$, with a phenyloxycarbonyl group, with an $R^{15}_a$—CO—O—($R^{16}_a CR^{17}_a$)—O—CO or with a group ($R^{18}_a O$)PO ($OR^{19}_a$) in which:

$R^{15}_a$ is a ($C_1–C_{15}$)alkyl group, a ($C_3–C_7$) cycloalkyl group, a phenyl group or a phenylalkyl group in which the alkyl is $C_1–C_3$, $R^{16}_a$ and $R^{17}_a$, which are identical or different, represent a hydrogen atom, a ($C_1–C_6$)alkyl group or alternatively one of the residues $R^{16}_a$ and $R^{17}_a$ represents a ($C_3–C_7$) cycloalkyl group or a phenyl group, $R^{18}_a$ and $R^{19}_a$, which are identical or different, represent a hydrogen atom, ($C_1–C_4$)alkyl groups, benzyl or phenyl groups, $R^3_a$ is a hydrogen atom, a ($C_1–C_7$)alkyl group or a ($C_4–C_7$) cycloalkyl group, $T_a$ is a hydrogen atom, a phenyl group or a 5-membered heteroaryl group attached via a carbon or nitrogen atom and comprising a nitrogen, oxygen or sulphur atom optionally substituted with an alkyl group, or comprising a nitrogen atom optionally substituted with an alkyl group as well as an additional sulphur, oxygen or nitrogen atom, or alternatively, when $Z_a$ represents a bond, $T_a$ is a protecting group for an amino group or the residues $(T^1_a T^2_a U_a)$—$(CH_2)_m$— or $T^3_a O$—, in which $T^1_a$ to $T^3_a$, which are identical or different, are phenyl or 6-membered heteroaryl groups attached via carbon atoms, which, depending on the case, comprise one or two nitrogen atoms, 5-membered heteroaryl groups attached via carbon or nitrogen atoms, comprising a nitrogen atom optionally substituted with an alkyl group, sulphur or oxygen, or comprising a nitrogen atom optionally substituted with an alkyl group as well as an additional nitrogen, sulphur or oxygen atom, in which a 1,4-butadienylene bridge may be made between two neighbouring carbon atoms of the 5- or 6-membered heteroaryl groups mentioned above in the definition of the Ta residues; the bicyclic aromatic or heteroaromatic rings thus constituted may also be attached to a carbon atom of the 1,4-butadienylene group and, moreover, not only the phenyl groups and the 5- or 6-membered heteroaryl groups but also the bicyclic aromatic or heteroaromatic rings may be mono- or disubstituted on the carbon skeleton with fluorine, chlorine, bromine or iodine atoms or with cyano, hyroxyl, amino, dimethylamino, diethylamino, N-ethylmethylamino, trifluoromethyl, trifluoromethoxy, trifluoromethylthio, acetylamino, propionylamino, methanesulphonylamino, methanesulphonyloxy, phenyl, phenylmethoxy, 2-phenylethoxy, alkyl or alkoxy groups or trisubstituted with an amino or hydroxyl group and two chlorine or bromine atoms or with a hydroxyl group and two alkyl or alkoxy groups, the substituents being identical or different, and the alkyl and alkoxy parts mentioned above comprising from 1 to 4 carbon atoms, hydrogen atoms, ($C_1–C_{12}$)alkyl groups, cycloalkyl groups having from 3 to 10 carbon atoms, bicycloalkyl or tricycloalkyl groups having from 6 to 12 carbon atoms or $T^1_a$ and $T^2_a$ together represent a linear-chain ($C_3–C_7$) alkylene group, $U_a$ is the group >CH in which the hydrogen atom may be replaced by an alkyl, phenyl, hydroxyl, alkoxy, alkanoyloxy, alkoxycarbonyl or alkanoylamino group, in which the alkyls or alkoxys mentioned above may comprise, depending on the case, from 1 to 3 carbon atoms and the alkanoyls mentioned above may comprise 2 or 3 carbon atoms, or alternatively the >CHCH$_2$—group or a nitrogen atom, m represents 0, 1, 2 or 3 or alternatively $T_a$ is a group $(T^1_a T^2_a U_a)$—$(CH_2)_{ma}$ in which $T^1_a$, $T^2_a$, $U_a$ and ma are as defined above, except that the mono- or bicyclic aromatic or heteroaromatic rings mentioned above for $T^1_a$ and $T^2_a$ are connected together by a bond or by a —CH$_2$—, —C(CH$_3$)$_2$—, —CH$_2$CH$_2$—, —CH=CH— or —NHCO— bridge, $Y_a$ is an oxygen atom or a group —NR$^4_a$ in which R$^4_a$ makes the definition mentioned above form $R^1_a$, it being possible for the residues of $R^1_a$ and of $R^4$a to be identical or different, and $Z_a$ is a single bond defined by a —CO—, —CH$_2$—, —SO— or —SO$_2$— group, and, except where otherwise mentioned, the alkyl and alkoxy parts mentioned above may comprise from 1 to 3 carbon atoms, and the tautomers, diastereomers, enantiomers, mixtures and salts described in WO 94/17035.

Among these compounds, (R)-N$^2$-(diphenylacetyl)-N-(phenylmethyl)argininamide, (R)-N$^2$-(diphenylacetyl)-N-[(4-methylphenyl)methyl]argininamide, (R)-N-(2-(4-hydroxyphenyl)ethyl-N$^2$-[[5-(2-phenylethoxy)-1H-indol-2-yl]carbonyl]argininamide, N-[(4-aminocarbonylaminophenyl)methyl]-N$^2$-(diphenylacetyl)argininamide, (R)-N-[(4-hydroxyphenyl)methyl]-N$^2$-[[5-(2-phenylethoxy)-1H-indol-2-yl]carbonyl]argininamide, (R)-N$^2$-(diphenylacetyl)-N-[(4-fluorophenyl)methyl]argininamide, (R)-N-[(4-bromophenyl)methyl-N$^2$-(diphenylacetyl)argininamide, (R)-N$^2$-(diphenylacetyl)-N-(2-phenylethyl)argininamide, the optically active diastereoisomers of N$^2$-(α-cyclopentylphenylacetyl)-N-(4-hydroxyphenyl)methyl]-D-argininamide, N-[[4-(dimethylamino)phenyl]methyl]-N$^2$-(diphenylacetyl)argininamide, (R)-N$^2$-(diphenylacetyl)-N-[[4-(hydroxymethyl)phenyl]ethyl]argininamide, (R)-N$^2$-(diphenylacetyl)-N-[[4-(1-oxoethyl)phenyl]methyl]argininamide, (R)-N-[(4-chlorophenyl)methyl]-N$^2$-(diphenylacetyl)argininamide, (R)-N$^2$-(diphenylacetyl)-N-[[4-[(methylaminocarbonyl)amino]phenyl]methyl]argininamide, (R)-N-[(4-amino-3,5-dichlorophenyl)methyl]-N$^2$-(diphenylacetyl)argininamide, (R)-N-[(4-amino-3,5-dichlorophenyl)methyl]-N$^2$-(3,3-diphenyl-1-oxopropyl)argininamide, (R)-N-[(4-amino-3,5-dichlorophenyl)methyl]-N$^2$-(3,4-dichlorobenzoyl)argininamide, N$^2$-(diphenylacetyl)-N-[3-[1-[2-[5,11-dihydro-6(6H)oxopyrido[2,3-b][1,4]benzodiazepin-5-yl]-2-oxoethyl]-4-piperidyl]propyl]argininamide, N$^2$-(diphenylacetyl)-N-[(4-hydroxy-3-methoxyphenyl)methyl]argininamide, N$^2$-(diphenylacetyl)-N-[(3-hydroxy-4-methoxyphenyl)methyl]argininamide, (R,S)-N-[(4-amino-3,5-dibromophenyl)methyl]-N$^6$-(aminoiminomethyl)-N$^2$-(diphenylacetyl)lysinamide, N-[(3,5-dimethyl-4-hydroxyphenyl)methyl]-N$^2$-(diphenylacetyl)argininamide, N-[(1H-benzimidazol-5-yl)methyl]-N$^2$-(diphenylacetyl)argininamide, N$^2$-(diphenylacetyl)-N-[(4-hydroxy-3-methylphenyl)methyl]argininamide, N-[[4-(aminocarbonyl)phenyl]methyl]-N$^2$-(diphenylacetyl)argininamide, (R,S)-N$^6$-(aminoiminomethyl)-N$^2$-(diphenylacetyl)-N-[(4-hydroxyphenyl)methyl]lysinamide, (R)-N-[(4-hydroxyphenyl)methyl]-N$^2$-(phenylacetyl)argininamide, N$^2$-(diphenylacetyl)-N-[(1H-indol-5-yl)methyl]argininamide, (R)-N-[[4-(aminosulphonyl)phenyl]methyl)-N$^2$-(diphenylacetyl)argininamide, (R)-N$^2$-(diphenylacetyl)-N-[[4-methoxycarbonyl)phenyl)methyl]argininamide, (R)-N$^2$-(diphenylacetyl)-N-[(4-pyridyl)methyl]argininamide, (R)-N-[(4-amino-3,5-dibromophenyl)methyl]-N$^2$-(diphenylacetyl)argininamide, (R)-N$^2$-(diphenylacetyl)-N-C(2-thienyl)methyl]-N$^2$-(2-naphthoyl)argininamide, (R)-N-[(4-amino-3,5-dichlorophenyl)methyl]-N$^2$-(2-naphthoyl)argininamide, (R,S)-N$^5$-(4,5-dihydro-1H-imidazol-2-yl)-N$^2$-(diphenylacetyl)-N-[(4-hydroxyphenyl)methyl]ornithinamide, (R,S)-N$^2$-(diphenylacetyl)-N-[(4-hydroxyphenyl)methyl]-N$^5$-(1H-imidazol-2-yl)ornithinamide, (R)-N-([3-[(1,2-dihydro-3,5(4H)dioxo-1,2-diphenyl-3H-1,2,4-triazol-4-yl)methyl]phenyl]-N$^2$-diphenylacetyl)argininamide, N$^2$-(diphenylacetyl)-N-[(3-hydroxyphenyl)methyl]argininamide, (R)-N-[[3-[(4,5-dihydro-2,4(3H)dioxo-5,5-diphenyl-1H-imidazol-3-yl)methyl]phenyl]methyl]-N$^2$-(diphenylacetyl)argininamide, (R)-N$^2$-(diphenylacetyl)-N-[(4-hydroxyphenyl)methyl]argininamide, known under the code BIBP3226, N$^2$-(diphenylacetyl)-N-[2-(4-hydroxyphenyl)ethyl]argininamide, N$^2$-(diphenylacetyl)-[(4'-hydroxy-[1,1'-biphenyl]-4-yl)methyl]argininamide, N-[4-[(1,2-dihydro-3,5(4H)dioxo-1,2-diphenyl-3H-1,2,4-triazol-4-yl)methyl]phenyl]methyl]-N$^2$-(diphenylacetyl)argininamide, N$^2$-(diphenylacetyl)-N-[(4-methoxyphenyl)methyl]argininamide, N$^2$-(diphenylacetyl)-N-[2-(4-methoxyphenyl)ethyl]argininamide, N$^2$ (diphenylacetyl)-N-[2-(3-methoxyphenyl)ethyl]argininamide, N$^2$-(diphenylacetyl)-N-[(3-methoxyphenyl)methyl]argininamide, (R,S)-3-[4-(aminoiminomethyl)phenyl]-N$^2$-(diphenylacetyl)-N-[(4-hydroxyphenyl)methyl]alaninamide, (R,S)-3-[3-(aminoiminomethyl)phenyl]-N$^2$-(diphenylacetyl)-N-[(4-methoxyphenyl)methyl]alaninamide, (R,S)-3-[3-(aminoiminomethyl)phenyl]-N$^2$-(diphenylacetyl)-N-[(4-hydroxyphenyl)methyl]alaninamide, (R)-N$^2$-[bis(4-bromophenyl)acetyl]-N-[(4-hydroxyphenyl)methyl]argininamide, (R)-N$^2$-(diphenylacetyl)-N-[(4-ethoxyphenyl)methyl]argininamide, (R)-N$^2$ (diphenylacetyl)-N-[(4-hydroxyphenyl)methyl]-N-methyl]argininamide, (R,S)-N-[(4-amino-3,5-dibromophenyl)methyl]-3-[3-(aminoiminomethyl)phenyl]-N$^2$-(diphenylacetyl)alaninamide, (R)-N-[(4-hydroxyphenyl)methyl]-N$^2$-(2-naphthoyl)argininamide, (R)-N-[(4-hydroxyphenyl)methyl]-N$^2$-(2-naphthoyl)argininamide, (R)-N$^2$-(2,2-diphenyl-2-hydroxyacetyl)-N-[(4-hydroxyphenyl)methyl]argininamide, (R,S)-N$^2$-(diphenylacetyl)-N$^5$-(1-imidazol-2-yl)-N-[(4-methoxyphenyl)methyl)ornithinamide, (R,S)-3-[3-aminoiminomethyl)phenyl]-N$^2$-[[(diphenylmethyl)amino]carbonyl]-N-[(4-hydroxyphenyl)methyl]alaninamide, (R,S)-N$^2$-(diphenylacetyl)-N$^5$-(1H-imidazol-2-yl)-N-(phenylmethyl)ornithinamine, (R,S)-N-[(4-amino-3,5-dichlorophenyl)methyl]-N$^2$-(diphenylacetyl)-N$^5$-(1H-imidazol-2-yl)ornithinamide, (R,S)-N-[(4-hydroxyphenyl)methyl]-N$^5$-(1H-imidazol-2-yl)-N$^2$-(2-naphthoyl)ornithinamide, (R,S)-N$^2$-[[(diphenylmethyl)amino]carbonyl]-N-[(4-hydroxyphenyl)methyl]-N$^5$-(1H-imidazol-2-yl)ornithinamide, (R,S)-N-[(4-hydroxyphenyl)methyl]-N$^5$-(1H-imidazol-2-yl)-N$^2$-[(2-naphthyl)acetyl]ornithinamide, (R,S)-N-[(4-hydroxyphenyl)methyl]-N$^5$-(1H-imidazol-2-yl)-N$^2$-[(2-naphthyl)amino]carbonyl]ornithinamide, (R,S)-N-[(4-hydroxyphenyl)methyl]-N$^5$-(1H-imidazol-2-yl)-N$^2$-[(1,2,3,4-tetrahydroquinolin-3-yl)carbonyl]ornithinamide, (R,S)-N-[(4-hydroxyphenyl)methyl]-N$^5$-(1H-imidazol-2-yl)-N$^2$-[(1,2,3,4-tetrahydroquinolin-2-yl)carbonyl]ornithinamide, (R)-N-[(4-aminosulphonylaminophenyl)methyl]-N$^2$-(diphenylacetyl)argininamide, (R)-N-[(4-aminophenyl)methyl]-N$^2$-(diphenylacetyl)argininamide, (R)-N-[(6-quinolinyl)methyl]-N$^2$-(diphenylacetyl)argininamide, (R)-N$^2$-[(3,4-dichlorophenyl)acetyl]-N-[(4-hydroxyphenyl)methyl]argininamide, (R)-N$^2$-(diphenylacetyl)-N-[[4-(2-hydroxyethyl)phenyl]methyl]argininamide, (R,S)-N$^5$-(3-amino-1,2,4-oxadiazol-5-yl)-N$^2$-(diphenylacetyl)-N-[(4-hydroxyphenyl)methyl]ornithinamide, (R)-N$^2$-[(9-fluorenyl)carbonyl]-N-[(4-hydroxyphenyl)methyl]argininamide, (R,S)-6-(aminoiminomethyl)-$N^2$(diphenylacetyl)-N-[(4-hydroxyphenyl)methyl]norleucinamide, (R,S)-3-[4-(4,5-dihydro-1H-imidazol-2-yl)phenyl-$N^2$-(diphenylacetyl)-N-[(4-hydroxyphenyl)methyl]alaninamide, (R,S)-3-[3-(aminoiminomethyl)phenyl]-$N^2$-(diphenylacetyl)-N-[(4-ethoxycarbonyloxyphenyl)methyl]alaninamide, (R,S)-N-(2-(1,2-dihydro-1,2-diphenyl-3,5(4H)dioxo-1,2,4-triazol-4-yl)ethyl]-$N^2$-(diphenylacetyl)argininamide, (R,S)-$N^2$-(diphenylacetyl)-N-[(4-hydroxyphenyl)methyl]-2-methylargininamide, (R,S)-$N^2$-(diphenylacetyl)-N-[4-(3-hydroxypropyl)phenyl]methyl]argininamide, (R)-N-[[4-[(4,5-dihydro-5,5-dimethyl-2,4(3H)dioxo-1H-imidazol-3-yl)methyl]phenyl]methyl]-$N^2$-(diphenylacetyl)argininamide, are advantageous, BIBP 3226 being preferred.

VIII—Compounds of formula

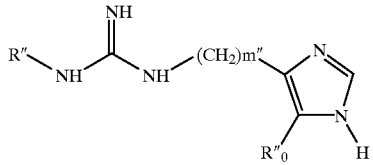

(VII)

in which R" is defined by the formula:

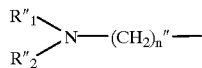

in which $R''_1$ represents a phenyl group unsubstituted or substituted with one or two halogen atoms, a $(C_1-C_3)$alkyl group or a pyridyl group unsubstituted or substituted with one or two halogen atoms, a $(C_1-C_3)$alkyl group or a $(C_1-C_3)$alkoxy group, $R''_2$ represents a hydrogen atom, a $(C_1-C_3)$alkyl group, a phenyl group optionally substituted with one or two halogen atoms or with a $(C_1-C_3)$alkyl group or with a $(C_1-C_3)$alkoxy group, a benzyl or heteroaryl group unsubstituted or substituted with one or two halogen atoms or a $(C_1-C_3)$alkyl or $(C_1-C_3)$alkoxy group, n" represents 1, 2, 3 or 4 or in which R" is defined by the formula:

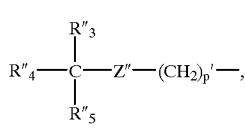

in which $R''_3$ represents a pyridyl ring unsubstituted or substituted with one or two halogen atoms, with a $(C_1-C_3)$alkyl or $(C_1-C_3)$alkoxy group, $R''_4$ represents a hydrogen atom or a phenyl group optionally substituted with one or two halogen atoms or with a $(C_1-C_3)$alkyl group or with a $(C_1-C_3)$alkoxy group, $R''_5$ represents a hydrogen. atom or a methyl or hyroxyl group and Z" represents a single bond, an oxygen atom or a sulphur atom and p" represents 1, 2 or 3, m" represents 1, 2 or 3 and $R''_0$ represents a hydrogen atom or a methyl group, as well as the pharmaceutically acceptable salts thereof, the NPY-antagonist effect of which is described in EP 448,765.

Among these compounds, those of formula (VII) in which m" is 3, $R''_0$ is hydrogen and R" is 2-(3-pyridyl-methylthio)ethyl, 3,3-diphenylpropyl, 2-(2-pyridylamino)ethyl, 2-(5-bromo-3-methyl-2-pyridylamino)ethyl, 2-(diphenylmethoxy)ethyl, 3-(3,5-difluorophenyl)-3-(2-pyridyl)propyl, 2-[N-(5-bromo-3-methyl-2-pyridyl)-N-benzylamino]ethyl or 2-(5-bromo-3-methyl-2-pyridyl)ethyl and the salts thereof are particularly advantageous, 1-[3-(3,5-difluorophenyl)-3-(2-pyridyl)]propyl-3-[4-(1H)imidazolyl]guanidine trihydrochloride (He 90481) being preferred.

IX—Dihydropyridines of formula:

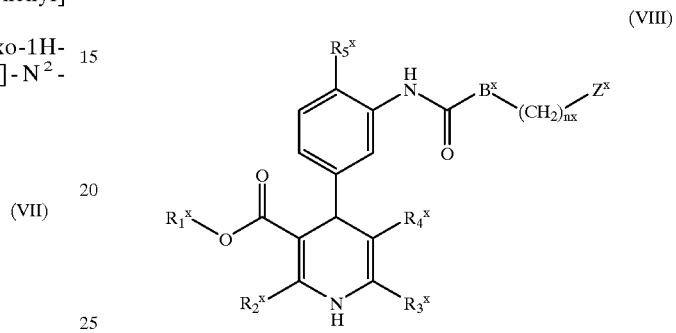

(VIII)

in which $R_1^x$ is a lower alkyl;

$R_2^x$ and $R_3^x$ are selected independently, from a cyano and a lower alkyl;

$R_4^x$ is selected from —$CO_2R_1^x$, cyano and

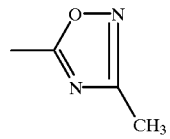

$R_5^x$ is selected from a hydrogen, a halogen, a hydroxyl, a lower alkyl, a lower alkenyloxy and a lower alkoxy;

$B^x$ is —NH— or a covalent bond;

nx represents an integer from 2 to 5 and $Z^x$ is selected from the group consisting of:

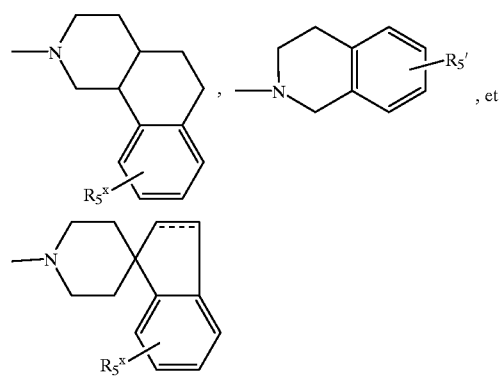

the solid or dotted lines representing a single or double bond, as well as the additional salts or solvates thereof described in U.S. Pat. No. 5,554,621.

B. Other NPY antagonists which are advantageous in the cosmetic compositions of the present invention are peptides chosen from those of groups IX to XII below.

X—Compounds of formula

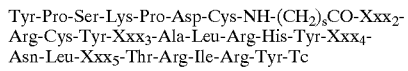                                      (IX)

in which

Xxx$_2$ and Xxx$_3$ are Ser or Ala, Xxx$_4$ and Xxx$_5$ are Leu, Ile, Met, Nle (norleucine) or Val Tc is OH, O(C$_1$–C$_4$)alkyl, NH$_2$ or NH(C$_1$–C$_4$)alkyl, s is an integer from 1 to 11, and the salts thereof, described in EP 355,794.

Among these compounds, that of formula (IX), in which s is 7, Xxx$_2$ is Ala, Xxx$_3$ is Ser, Xxx$_4$ and Xxx$_5$ are both Ile and Tc is NH$_2$, and the salts thereof, are advantageous.

XI—Compounds of formula

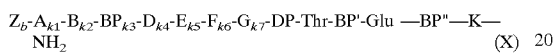   (X)

in which k$_1$, k$_2$, k$_3$, k$_4$, k$_5$, k$_6$ and k$_7$ represent zero or 1, their sum being at least 1, A is Phe or Tyr; B is Pro, Ser, Ala, Gly, Abu, Cys, Pro-Ser, Cys-Ser, Ala-Ser, Gly-Ser, Abu-Ser or Pro-Ala, Abu being 2-aminobutyric acid; BP, BP' and BP'' are amino acids with a basic side chain;

D is Pro or Cys; E is NH-(CH$_2$)$_t$-CO, t being 0–10; F is Cys, Abu, Gly or Ala; G is Ile-Asn, Leu-Asn, Val-Asn or Asn; DP is the residue of a dipeptide formed by lipophilic amino acids; k is Phe or Tyr; Z$_b$ is hydrogen, an amino-protecting group or a benzyl group, (C$_2$–C$_{10}$)acyl or (C$_1$–C$_5$) alkyl and in which two Cys radicals can be linked via a disulphide bridge, as well as the salts thereof, described in DE 3,939,801.

Among these compounds, those of Formula (X) in which BP is Lys or Arg; E is NH-(CH$_2$)t-CO, with t=1–7; F is Cys or Abu; G is Ile-Asn or Asn; DP is Leu-Ile, BP'and BP'', which are identical, are Arg; Zb is hydrogen, acetyl or a group

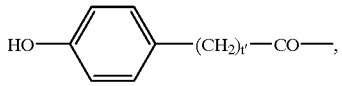

where t' is 0, 1 or 2, and the salts thereof, are advantageous, the compound of formula

   (X')

where Aoc represents 8-aminooctanoic acid being particularly preferred.

XII—Cyclic or linear compounds of formula

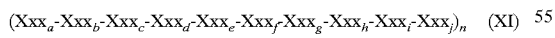   (XI)

in which Xxx$_a$, Xxx$_b$, Xxx$_c$ and Xxx$_j$ either do not exist, or alternatively Xxx$_a$ is P$_1$ or Cys; Xxx$_b$ is Cys, P$_1$ or one or two amino acids; Xxx$_c$ is P1, Cys, Ser, Thr, Ala or Gly; Xxx$_d$ is R$_1$, Cys, Ser, Thr, Ala or Gly; Xxx$_e$ is Leu, Ile, Val or Nle; Xxx$_g$ is Arg, Lys or His; Xxx$_g$ is Arg, Lys, His, Val, Leu, Ile or Nle; Xxx$_h$ is Tyr, Phe, Trp, His, Lys or Arg; Xxx$_i$ represents an NH$_2$ group or an ester group or alternatively one or two amino acids; Xxx$_j$ is Cys or P$_2$;l P$_1$ is hydrogen or a group P—CO where P is hydrogen, a glycosyl, nucleosyl or lipolyl radical or a (C$_1$–C$_{20}$)alkyl group, optionally containing double bonds and substituents selected from halogens and the NO$_2$, NH$_2$, OH, sulpho, phospho, carboxyl and alkyl groups; P$_2$ is a group NP$_{12}$P$_{13}$ or OP$_{14}$ in which P$_{12}$ and P$_{13}$ represent hydrogen or an alkyl, cycloalkyl, N-glycosyl, N-lipolyl, aralkyl or aryl group, optionally substituted with a halogen or with an NO$_2$, NH$_2$, OH, sulpho, phospho, carboxyl or alkyl group; and P$_{14}$ represents hydrogen or an alkyl, cycloalkyl, aralkyl, -O-glycosyl, -O-lipolyl, aralkyl or aryl group, optionally subsititued with a halogen or with an NO$_2$, NH$_2$, OH, sulpho, phospho, carboxyl or alkyl group, with the limitation that when Xxx$_b$ does not exist or represents Cys or P$_1$, then Xxx$_a$ is nonexistent, when Xxx$_d$ is Cys or P$_1$, then Xxx$_c$ is nonexistent, when Xxx$_i$ is NH$_2$ or an ester, then Xxx$_j$ is nonexistent.

These compounds are described in WO 93/12139.

Among these, the peptide of formula:

   (XI')

known under the code number BRC 672, is particularly advantageous.

XIII—Compounds of formula

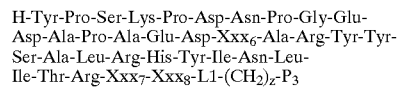   (XII)

in which z is 0, 1 or 2, Xxx$_6$ is Met or Leu; Xxx$_7$ is Glu, (R)-Glu, Pro or (R)-Pro; Xxx$_8$ is Arg, (R)-Arg or (R,S)-Arg; L$_1$ is O or NP', P' being H or alkyl; and P$_3$ is a phenyl or naphthyl group which is unsubstituted or substituted with one or two F, Cl, Br, alkyl, phenyl, OH, (phenyl)alkoxy, alkylcarbonyl, NH$_2$ (optionally substituted with one or two alkyls), alkylsulphonyl, alkyl- or alkoxycarbonylamino, COOH, alkoxycarbonyl, NH$_2$CO (optionally substituted with one or two alkyls), alkylcarbonyloxy, alkylsulphonyloxy, CH$_2$OH, 1- or 2-hydroxyethyl, (alkyl)aminosulphonyl, cyanamino, aminocarbonylamino (optionally substituted with one or two alkyls) or NH$_2$C(=N.CN)NH;

a 5-membered aromatic heterocycle containing oxygen, sulphur or nitrogen, an imino group or an imino group containing oxygen, sulphur or nitrogen;

a 6-membered aromatic heterocycle with one or two nitrogen atoms; it being possible for the said heterocycles to be C-substituted with (C$_1$C$_6$)alkyl or with phenylalkyl and optionally fused with benzene and optionally also substituted either with an F, Cl, Br, (C$_1$–C$_6$)alkyl, alkoxy, OH, phenyl, NO$_2$, NH$_2$ (optionally substituted with one or two alkyls or with an alkanoyl), CN, COOH, alkoxycarbonyl, NH$_2$CO (optionally substituted with one or two alkyls), CH$_2$F, CHF$_2$, CF$_3$, alkanoyl or NH$_2$SO$_2$ (optionally substituted with one or two alkyls), or with two F, Cl, Br, methyl, methoxy or OH;

a phenyl group substituted with a [1,5-dihydro-2,4(3H) dioxoimidazol-3-yl]alkyl group or with a [dihydro-3,5 (4H)dioxo-3H-1,2,4-triazol-4-yl]alkyl group in which the imidazole and triazole groups may be substituted with one or two phenyls; the alkyl and alkoxy groups containing from 1 to 3 carbon atoms, and the salts thereof.

These compounds are illustrated in DE 4,311,756.

XIV—NPY antagonists which can be prepared according to WO 94/00486, JP 06-116284, JP 07-267988, DE 3,811,193, U.S. Pat. No. 5,328,899 and WO 95/00161, such as compound (XIII)

$$\text{CH}_3\text{CO-D-Cys-Leu-Ile-Thr-Arg-Cys-Arg-Tyr-NH}_2 \quad (XIII)$$
(with a disulfide bridge between the two Cys residues)

described in JP 06-116 284 and compound (XIV)

$$\begin{array}{c}\text{Ile-Cys-Pro-Cys-Tyr-Arg-Leu-Arg-Tyr-NH}_2\\ |\quad\quad |\\ \text{Ile-Cys-Pro-Cys-Tyr-Arg-Leu-Arg-Tyr-NH}_2\end{array} \quad (XIV)$$

described in WO 94/00486.

C. NPY-antagonist products, in particular extracts with NPY-antagonist activity, which can be obtained by extraction of cells or tissues of animal or plant origin or by fermentation of microorganisms, in particular bacteria and fungi, for example yeasts, are advantageous NPY-antagonist components in the cosmetic compositions of the present invention.

Particularly advantageous and even preferred products of this class are the products of groups XV, XVI and XVII illustrated below.

XV—Extracts with NPY-antagonist activity obtained by extraction of a sponge, Orina sp. Gray (or Gellius sp.), in particular the indole compounds described in J. Nat. Products, 1994, 57, 1294–1299 and ibid. 1995, 58, 8, 1254–1260, or mixtures thereof, more particularly gelliusine A, gelliusine B, 2-[5-hydroxy-3-(2-aminoethyl)]indol-2-yl-6-bromo-3-indolethanamine and 2-[6-bromo-3-(2-aminoethyl]indol-2-yl-6-bromo-3-indolethanamine, and the salts and mixtures thereof.

XVI—Extracts from fermentation of Aspergillus strains, for example of *Aspergillus niger* with NPY-antagonist activity, in particular the compound known under the code name BMS-192548, which can be prepared by extraction of the culture medium of *Aspergillus niger* WB 2346, as described in J. Antibiotics, 1995, 48, 10, 1055–1059, having the formula (XV)

[Structure (XV): a tetracyclic compound with OH, OCH$_3$, and acetyl (COCH$_3$) substituents]

XVII—Products, in particular extracts obtained by fermentation of Actinomycetaceae strains, having NPY-antagonist activity. More particularly, extracts obtained from a novel strain of actinomycetes having a particularly advantageous activity as NPY-receptor antagonists are particularly preferred NPY-antagonist components.

Fractions with NPY receptor antagonist activity are obtained from the fermentation broths of this strain, by filtration of the supernatant, optionally followed by steps of concentration, purification and/or lyophilization, these fractions being devoid of genotoxicity and having a stability which is sufficient to allow them to be formulated in the cosmetic compositions of the present invention.

The supernatant of the fermentation broth can also be used as it is.

These novel extracts constitute a subsequent and particularly advantageous aspect of the present invention.

The organism producing the extracts with NPY receptor antagonist activity according to this specific aspect of the present invention is an actinomycetes strain which has been isolated from a sample of grassland taken from the Haute Garonne (France), which has been assigned the in-house number SEBR 2794. A sample of this microorganism was deposited on Jul. 13, 1993 at the CNCM of the Pasteur Institute where it was registered under the reference I 1332.

The biochemical characteristics of this microorganism were determined on API 50 CH (specific for sugars), API 50 AO (specific for organic acids) and API 50 AA (specific for amino acids) kits, (marketed by BioMerieux for API 50 CH and by the API Research Laboratory for the others). It was thus determined that this microorganism belongs to the family of Streptomycetaceae, genus Streptomyces.

This is a polymorphous, filamentous microorganism. It grows well at 28° C. on an ISP$_2$ culture medium (agar yeast malt extract), the colour of its vegetative mycelium being pinkish-grey.

This organism, which has properties that did not allow it to be identified as a species already described, must be considered as a novel species and it has been designated as Streptomyces sp SEBR 2794.

The strain Streptomyces sp SEBR 2794, deposited at the CNCM of the Pasteur Institute under the number I 1332, and productive mutants thereof, also constitute a subject of the present invention.

This novel strain was isolated according to the usual method, which consists in placing a small amount of soil in suspension in distilled water, in diluting the suspension to different concentrations and in plating out a small volume of each dilution on the surface of a Petri dish containing a nutrient agar medium. After incubating for a few days at 28° C., which allows the microorganisms to grow, the various colonies are taken separately and subcultured on nutrient agar so as to obtain more abundant cultures therefrom. After culturing on nutrient agar medium and subculturing several times successively, which makes it possible to obtain an abundant and pure culture of the strain of interest, a batch 0 for storage of the parent strain is manufactured, followed by primary and secondary inoculation batches.

For this, a suspension of spores is prepared from a culture on nutrient agar medium in a Petri dish and from maintenance medium; this medium contains a cryoprotective agent making it possible to ensure good viability of the spores during conservation by freezing.

The suspension of spores obtained is divided into cryotubes which will be stored at –80° C.; these tubes constitute the batch 0.

Following the same procedure, but starting with a tube from batch 0, a primary inoculation batch is prepared.

Next, still according to the same procedure, a secondary inoculation batch is prepared from a cryotube of the primary inoculation batch.

The manufacture of the inoculation batches 0, 1 and 2 ensures long-lasting accessibility of the strain and thus of the desired activity.

The process for preparing the extracts with NPY receptor antagonist activity consists essentially in cultivating the novel strain SEBR 2794, or productive mutants thereof, on a suitable medium and under suitable culture conditions and in then extracting from the fermentation broth the active fraction produced during the culturing; this active fraction is found in the supernatant.

Streptomyces sp SEBR 2794 can be cultured by any aerobic culture method. For this purpose, the various types of apparatus which are in common use in the fermentation industry are used. It is possible, in particular, to adopt the following approach for carrying out the operations.

Starting with a tube of the secondary inoculation batch, Petri dishes are seeded and, after incubating for five days, these provided a suspension of spores.

This suspension of spores is used to seed stirred conical flasks containing a suitable medium. The stirred flask can also be seeded directly with a tube of the inoculation batch. The culturing in stirred flasks can last for two to seven days but a duration of three to five days is preferred.

The production of activity is observed in the supernatant, from the first stage and onwards of culturing in flasks, but it may be advantageous to perform two successive culturing stages: a first stage for propagating the biomass, a second for production. In the latter case, a duration of one or two days is sufficient for the first stage.

The antagonist activity contained in the flask culture supernatants is expressed as $ID_{50}$ (50% inhibitory dilution, namely the dilution which inhibits binding of the ligand to its receptors by 50%); the $ID_{50}$ is generally between $\frac{1}{200}$ and $\frac{1}{1000}$.

The NPY receptor antagonist activity is obtained in the supernatant of the flask cultures, but it appears to be advantageous, in order to obtain a higher activity, to perform culturing in a fermenter and then to extract the supernatant therefrom. The fermenter is seeded with a one- or two-day-old stirred flask culture. In the fermenter, depending on the culture medium used, the antagonist activity may be observed in the supernatant from the first day onwards, but it is advantageous to prolong the culturing beyond three days in order to obtain an optimal production.

Culturing SEBR 2794 in a fermenter makes it possible to control better the culture conditions which are described below, such as, for example, the pH or the aeration.

The antagonist activity obtained in the fermenter supernatants, before concentrating, may vary, according to the culture conditions applied, between an $ID_{50}$ of 1/500 and an $ID_{50}$ of 1/10000.

The culture medium used in the fermentation process must contain at least one assimilable carbon source, an assimilable nitrogen source and mineral elements. Assimilable carbon sources which may be used are carbohydrates such as glucose, mannose, maltose, dextrins, glycerol, amino acids and proteins. Assimilable carbon sources which may also be used are acetic acid, suberic acid, citric acid, propionic acid, succinic acid and 2-ketoglutaric acid or certain animal or plant oils.

Proteins, peptones and amino acids are among the best sources of assimilable nitrogen. These sources comprise, for example, casein, lactalbumin, gluten and hydrolysates thereof, fish meal, yeast extracts and peptones.

The production of biomass may be increased by the addition, during culturing, of one and/or the other of these two main substrates.

Potassium, sodium, iron, magnesium, calcium and manganese salts are among the mineral elements added to the culture medium to ensure growth of the microorganism and to optimize the assimilation of the carbon and nitrogen sources by the cells of the microorganism, as well as phosphorus compounds such as phosphates and trace elements.

To grow the SEBR 2794 source on a medium containing these components, the process of culturing under aeration and with stirring, in which a liquid medium is used, is advantageous, although culturing on an agar medium can also be used.

The temperature, the duration of incubation, the aeration and the pH of the medium must be such that they give rise to maximum growth of the microorganism used and a maximum yield of extracts with NPY receptor antagonist activity; a culture stirred for about 2 to 7 days is usually advantageous.

The pH of the culture medium is preferably maintained at a more or less neutral or very weakly basic value and the optimum incubation temperature is between about 23° C. and 35° C., the preferred range being 25° C. to 33° C.

The culture conditions, such as the composition and pH of the medium, the incubation temperature, the stirring speed and the aeration of the fermentation may vary within a wide range and should obviously be chosen so as to obtain the best possible results.

In order to obtain extracts of the NPY receptor antagonists produced during the culturing, the supernatant is separated from the mycelium after the fermentation broth has or has not been frozen. For this separation, centrifugation, filter-press filtration or clarifying filtration, that is to say filtration in the presence of a filtering adjuvant, or any other technique usually used to extract an extracellular product from a fermentation broth can be used.

The active extract for cosmetic use is prepared from the culture supernatant obtained.

The supernatant may be concentrated by a membrane technique or by any other concentration method so as to facilitate the packaging or the use of the active solution.

It is thus possible to obtain activities with $ID_{50}$ values ranging from 1/250 to 1/50000.

Whether it has been concentrated or not, the supernatant may be diluted in various solvents which are compatible with cosmetological use.

The extract thus obtained according to this specific aspect of the present invention is filtered through a 0.2 μm filter in order to remove all trace of residual biomass and to ensure microbiological cleanliness: it is then packaged aseptically in sterile bottles and the active solution which can be used in cosmetology is obtained.

Fluids containing the NPY-antagonist extracts of the present invention in a glycol, preferably in propylene glycol, constitute another very advantageous aspect of the present invention. If it is desired to obtain a powder instead of an active solution, the filtrate can simply be lyophilized.

An assay of NPY receptor antagonist activity carried out on an aliquot makes it possible to evaluate the activity of the active solution and to check the reproducibility of the process.

On the supernatant or the lyophilizate, the extract of the invention may be purified in a more or less thorough manner according to the conventional techniques for purifying "biomolecules", polymers, protein substances or the like, such as, for example, gel permeation chromatography, ultrafiltration, adsorption chromatography, countercurrent chromatography or electro-focalization.

The extracts obtained from this novel strain have a very advantageous NPY receptor antagonist activity. Their strong affinity for these receptors, both for the Y1 and Y2 subtypes, has been demonstrated in dog adipocytes, this model displaying great homology with human adipocyte. More particularly, the adipocyte membranes were obtained from omental adipose tissue taken from dogs, essentially used in the technique described by Taouis et al., J. Pharmacol. Exp. Ther (1987), 242, 1041–1049. The binding studies were performed according to the known conventional techniques. In particular, the adipocyte membranes (200 μg/ml) are incubated for 60 minutes at 30° C. in a buffered binding medium (20 mM Krebs-Ringer Hepes solution, pH=7.4, 1% bovine serum albumin, 0.25 mg/ml bacitracin) with 0.08 nM of [$^{125}$I]-NPY labelled with the Bolton-Hunter reagent (Amersham IM 170.2000 Ci/mmol) in the presence or absence of 0.3 µM pig NPY. The incubation is stopped by filtration using Whatman GF/C filters and the radioactivity retained by the filter is evaluated with a gamma counter.

The non-specific binding, measured in the presence of 0.3 µM unlabelled NPY, represents 25% of the total binding. The dog adipocyte membrane preparation carries $Y_1$ and $Y_2$ receptors which may be distinguished on the basis of the selective affinity of the NPY fragment (13–36) for the $Y_2$ receptors.

The extracts according to the present invention demonstrated good affinity for the NPY receptors of this tissue, by displacing the [$^{125}$I]-NPY bound to the adipocyte membranes in a dose-dependent manner with $IC_{50}$ values (that is to say concentrations which inhibit the specific binding of [125I]-NPY by 50%) which depend on the degree of purification of the extracts and which, in the case of the crude extracts obtained directly from the fermentation supernatants by lyophilization, are at least about $10^{-2}$ mg/ml.

The NPY-antagonist nature of the extracts according to this specific aspect of the present invention was demonstrated by studies on isolated organs and more particularly in the model of rat "vas deferens". The extracts showed antagonist properties towards the effects of NPY in Y2 models of rat vas deferens and were studied according to the procedure described in Regulatory Peptides 1986, 13, 307–318.

This activity was confirmed on human adipocytes isolated from subcutaneous adipose tissue, by assaying the release of fatty acids into the culture medium and comparing it with the control (incubation without product).

50% (w/w) solutions of these extracts in propylene glycol are particularly preferred.

The aseptic preparation of these solutions makes it possible to avoid the addition of preserving agent.

In the preparation of the compositions according to the present invention, the extracts with NPY receptor antagonist activity are mixed with aqueous or non-aqueous solvents and with conventional diluents which are compatible with topical use, as well as with the active components of the composition itself. Suitable solvents and/or diluents will be chosen according to their capacity to transport the active component from the extract of the invention into the subcutaneous adipose layer.

These compositions generally contain excipients or additives chosen from the ingredients usually used in compositions intended for local application according to the need for the specific formulations envisaged.

They may contain, for example, thickeners, softeners, emollients, stabilizers, preserving agents, anti-foaming agents, surfactants, antioxidants, dyes and/or pigments, and fragrances.

They may also contain other active components having either an effect of the same type, for example products which contribute towards controlling lipolysis/ lipogenesis or products which are useful in this type of composition, such as collagen synthesis stimulators, collagenase or elastase inhibitors, and vasoprotectors.

The preferred cosmetic compositions according to the present invention contain, besides the NPY antagonist, an α2-antagonist which may itself also be a non-peptide synthetic compound, a peptide or a product obtained by fermentation of a microorganism, for example a bacterium or a fungus, or by extraction of cells or tissues of plant or animal origin.

α2-Antagonists which are advantageous to use as additional components, along with the NPY antagonist, are those of classes D and E below.

D. Synthetic products chosen from those of groups XVIII to XXV below.

XVIII—The compounds described in BE 840,363, in particular mirtazapine.

XIX—The compounds described in DE 2,603,407, in particular setiptiline and structural analogues thereof.

XX—The compounds described in U.S. Pat. No. 4,337,260, in particular mosapramine XXI—The compounds described in U.S. Pat. No. 2,979,511, in particular idazoxan.

XXII—The compounds described in WO 92/13856, in particular 5-thiazolyl-N,N-dimethyltryptamines including CP 93393.

XXIII—The compounds described in U.S. Pat. No. 4,229, 449, in particular reboxetine.

XXIV—The compounds described in GB 2,157,631, in particular fluparoxan.

XXV—The compounds described in GB 2,167,408, in particular altipamezole.

E. α2-Antagonist products obtained by extraction of cells or tissues of animal or plant origin or by fermentation of microorganisms, in particular bacteria and fungi, for example yeasts. Examples of products of this class, also including semisynthetic products, are the products of-. groups XXVI and XXVII below.

XXVI—Extracts of ergot, components and semisynthetic compounds thereof, having an α2-antagonist action, in particular nicegoline.

XXVII—Products, in particular extracts obtained from the fermentation of strains of *Bacillus licheniformis*, with antagonist activity towards the α2 receptor, in particular from the strain SEBR 2464.

These products, in particular the extracts belonging to this group, represent another specific aspect of the present invention.

The productive organism according to this specific aspect of the present invention is a strain of *Bacillus licheniformis* which has been isolated and has been given the code number SEBR 2464. A sample of this microorganism was deposited on 22 October 1996 at the CNCM of the Pasteur Institute, where it was registered under the reference I-1778.

The characteristics of this microorganism were determined on

API 20B, API 50 CHB, 50 CH, 50 AA, 50AO and 20E API kits.

This is a bacterium in uniformly shaped mobile rod form, from 2 to 10 µm in length and from 0.5 to 1 µm in width, individually or in short chains.

As with most Bacilli, this bacterium is gram+, facultative anaerobic, catalase positive, oxidase negative and has the characteristic of sporulating under certain conditions.

It grows well at pH 5 to 7, at temperatures between 15 and 55° C. and for salinities (NaCl) of up to 7%.

This strain was isolated as a contaminant, during experiments using columns of sand, according to the conventional microbiological techniques known to those skilled in the art.

This particular strain, along with productive mutants thereof, therefore constitutes a further subject of the present invention.

After culturing on nutrient agar medium and subculturing several times successively, which make it possible to obtain an abundant and pure culture of the strain of interest, a batch 0 is manufactured for storage of the parent strain, followed by primary and secondary inoculation batches.

For this, a suspension of spores is prepared from a culture on nutrient agar medium in a Petri dish and from a maintenance medium; this medium contains a cryoprotective agent making it possible to ensure good viability of the spores during storage by freezing.

The suspension of spores obtained is divided into cryotubes which will be stored at −80° C.: these tubes constitute batch 0.

Following the same procedure, but starting with a tube from batch 0, a primary inoculation batch is prepared.

Next, still according to the same procedure, a secondary inoculation batch is prepared from a cryotube of the primary inoculation batch.

The manufacture of the inoculation batches 0, 1 and 2 ensures long-lasting accessibility of the strain and thus of the desired activity.

The process for preparing the extracts with α2-receptor antagonist activity consists essentially in growing the novel strain SEBR 2464, or productive mutants thereof, on a suitable medium and under suitable culture conditions and in then extracting the active fraction from in the culture supernatant.

This supernatant may be concentrated until a dry extract is obtained.

The Bacillus licheniformis SEBR 2464 can be cultured by any aerobic culture method and in various types of apparatus usually used in the fermentation industry. It is possible, in particular, to adopt the following approach for carrying out the operations.

Starting with a tube of the secondary inoculation batch, Petri dishes are seeded and, after incubating for two days, these allow stirred conical flasks containing a suitable medium to be inoculated.

A stirred flask can also be seeded directly with a tube of the inoculation batch. In this case, the duration of culturing will be longer for the same medium.

The antagonist activity is obtained in the flask cultures within 10 hours to 48 hours depending on the culture conditions used.

The α2-receptor antagonist activity is extracted from the culture supernatants. The activity of the extracts is expressed as $ID_{50}$ (50% inhibitory dilution); one liter of culture makes it possible to obtain 10 ml of extract having an $ID_{50}$ value of between 1/2500 and 1/10,000.

The α2-receptor antagonist activity may be obtained by extracting the supernatant of the flask cultures, but it appears to be advantageous, in order to obtain a higher activity, to perform culturing in a fermenter and then to extract the supernatant therefrom.

The fermenter is seeded with a 1- to 2-day-old culture in a stirred flask; it is preferable for the culture not to have begun to sporulate.

In the fermenter, according to the culture conditions used, the antagonist activity may be observed from the first hours of culturing and onwards, but it is advantageous to wait until the stationary growth phase has been reached before extracting.

Culturing SEBR 2464 in a fermenter allows better control of the culture conditions which are described below, for example the pH and the aeration.

The α2-receptor antagonist activity obtained in the fermenter may vary, depending on the culuture conditions applied.

One liter of culture makes it possible to obtain from the supernatant, after extraction, 10 ml of extract having an $ID_{50}$ of between 1/3000 and 1/15,000.

The characteristics of the medium are identical to those described above for the strain SEBR 2794.

In order to grow the strain SEBR 2464 on a medium containing these components, the process of culturing under aeration and with stirring, in which a liquid medium is used, is advantageous, although culturing on an agar medium can also be used.

The temperature, the duration of incubation, the aeration and the pH of the medium must be such that they give rise to a maximum growth of the microorganism used and a maximum yield of extract with a2-receptor antagonist activity.

A culture stirred and aerated for about 10 hours to 48 hours is usually advantageous.

The pH of the culture medium is preferably maintained at a more or less neutral or very weakly acidic value and the optimum incubation temperature is between 25° C. and 50° C.

The culture conditions, such as the composition and pH of the medium, the incubation temperature, the stirring speed and the aeration of the fermentation, may vary within a wide range and should obviously be chosen so as to obtain the best possible results.

The production of an extract having a high α2-receptor antagonist activity requires several extraction steps.

A first step consists in eliminating the biomass. For this, centrifugation, tangential microfiltration, clarifying filtration, that is to say a filtration in the presence of a filtering adjuvant, or any other method usually used to extract an extracellular product from a fermentation broth may be used. The supernatant is then placed in contact overnight with a hydrophobic resin preferably made of polystyrene-divinylbenzene, for example such as Amberlite $XAD_2$ resin (Rohm & Haas) or CHP20P resin (Mitsubishi).

The loaded resin is then separated by frontal filtration and the filtrate is removed.

The resin undergoes several successive extractions with different solvents, allowing molecules of a hydrophobic nature to be extracted. After each extraction, the resin is separated from the organic phase by filtration.

The various organic phases are then evaporated under vacuum, together or separately, until one or more dry extracts are obtained.

An assay of α2-receptor antagonist activity performed on an aliquot of each of the extracts makes it possible to evaluate their activity and to check the reproducibility of the process.

The dry extract thus obtained may be taken up in various solvents usually used in cosmetology.

The uptake concentration is chosen to allow complete dissolution of the extract and to be compatible with the subsequent use. In order to eliminate all trace of residual biomass and to ensure its microbiological stability, the extract is filtered on a 0.2 μm filter and divided aseptically into sterile flasks.

The α2-antagonist activity of the extracts was evaluated using the technique described by Chapleo CB et al., J. Med. Chem., 1983, 26, 823–831, on the in vitro displacement, in rat cortex, of the α2-receptor antagonist reference ligand: tritiated idazoxan.

The α2-antagonist extract, containing 30% dry extract, is introduced into a 50/50 propylene glycol/water mixture and makes a preferred dilution according to the invention.

Dilutions for aseptic preparation of these solutions, which makes it possible to avoid the addition of preserving agent, may also be used.

In the preparation of the compositions according to the present invention, the extracts thus made up with α2-receptor antagonist activity are mixed with aqueous or non-aqueous solvents and with conventional diluents which are compatible with a topical use, as well as with the active components of the composition itself. Suitable solvents and/or diluents will be chosen according to their capacity to transport the active component from the extract of the invention into the subcutaneous adipose layer.

These compositions generally contain excipients or additives chosen from the ingredients usually used in compositions intended for a local application, according to the need for the specific formulations envisaged.

They may contain, for example, thickeners, softeners, emollients, stabilizers, preserving agents, anti-foaming agents, surfactants, antioxidants, dyes and/or pigments, and fragrances.

They may also contain other active components having either an effect of the same type, for example products which contribute towards regulating lipolysis/lipogenesis, or products which are useful in this standard type of composition, such as collagen synthesis stimulators, collagenase or elastase inhibitors, or vasoprotectors.

The α2-antagonist extracts of the invention moreover proved to be completely devoid of genotoxicity in the Ames test and the test of DNA repair. Their stability is compatible with their use in cosmetic compositions.

The cosmetic compositions of the present invention contain the NPY antagonist in percentages of between 0.00001% to 5% relative to the total weight of the composition, mixed with the excipients commonly used to prepare cosmetic formulations to be applied to the skin.

The said percentages may vary within the range indicated above as a function of the intrinsic activity of the NPY-antagonist component included in the composition. Preferably, the said NPY-antagonist component is present in percentages of from 0.0001% to 2%.

The NPY-antagonist component is, advantageously chosen from the products included in classes A, B and C above, those of class C being particularly advantageous. The components belonging to groups XV, XVI and XVII are preferred.

In the preparation of the compositions according to the present invention, the NPY-antagonist component is mixed with aqueous or non-aqueous solvents and with conventional diluents which are compatible with use on the skin, as well as with other components of the composition itself. Suitable solvents and/or diluents will be chosen according to their capacity to deposit the NPY-antagonist active component of the invention onto the skin.

These compositions generally contain excipients or additives selected from the ingredients usually used in compositions intended for a local application according to the need for the specific formulations envisaged.

They may contain, for example, thickeners, softeners, emollients, stabilizers, preserving agents, anti-foaming agents, surfactants, antioxidants, dyes and/or pigments, and fragrances.

When the NPY-antagonist component is an extract of cells or tissues of animal or plant origin or a product, in particular an extract, obtained by fermentation of a microorganism, for example a bacterium or a fungus, the amount of NPY-antagonist component is always from 0.00001% to 5%, preferably from 0.0001 to 2%, relative to the total weight of the composition, the said amount being calculated relative to the weight of the dry extract.

The compositions according to the present invention comprise, according to a preferred aspect, an extract obtained by fermentation of the novel strain SEBR 2794 in proportions, on a weight/weight percentage basis, which depend on the degree of NPY receptor antagonist activity of the extract used and therefore on the concentration of dry substance and on the specific activity of this substance.

The higher the antagonist activity of the extract used towards the NPY receptors, the lower is the weight amount required to obtain the desired lipolytic effect, and vice versa.

In order to obtain the cosmetic compositions according to the invention, the crude extracts (supernatants filtered through a 0.2 μm filter) obtained directly from the fermentation may conveniently be used without any purification step, in proportions of between 0.00001 and 5%, advantageously from 0.0001 to 2%, better still from 0.01 to 2% by weight and preferably from 0.1 to 2% by weight. These weight percentages are, naturally, calculated on the basis of the weight of extract prepared.

When the compositions of the present invention also contain, in addition to the NPY-antagonist component, an α2-antagonist component, the latter is present in a percentage of from 0.00001 to 5%, advantageously from 0.0001 to 2%, better still from 0.001 to 1% and preferably from 0.01 to 0.5%, relative to the total weight of the composition.

The said percentages may vary within the ranges indicated above as a function of the intrinsic activity of the α2-antagonist component included in the composition.

The α2-antagonist component is advantageously chosen from the products included in classes D and E above, those of class E being particularly advantageous. The compounds belonging to group XXVII are preferred.

When the α2-antagonist component is an extract of cells or tissues of animal or plant origin or a product obtained by fermentation of a microorganism, for example a bacterium or a fungus, the amount of α2-antagonist component is that indicated above, the said amount being calculated on the basis of the weight of the dry extract.

According to an advantageous aspect of the present invention, the cosmetic composition contains both an NPY-antagonist component and an α2-antagonist component, the NPY-antagonist component being selected from those of classes A, B and C above and the α2-antagonist component being selected from those of classes D and E above.

According to a particularly advantageous aspect, the cosmetic composition of the present invention contains an NPY-antagonist component selected from those belonging to class C, in particular to groups XV, XVI and XVII and an α2-antagonist component selected from those belonging to class E, in particular to group XXVII.

According to a preferred aspect, the present invention relates to a cosmetic composition containing an NPY-antagonist component consisting of an extract selected from those of group XVII above and an a2-antagonist component consisting of an extract selected from those of group XXVII above.

More particularly, the composition according to this preferred aspect of the present invention contains an NPY-antagonist component which may be obtained by fermentation of the strain Streptomyces sp. SEBR 2794 deposited at the CNCM of the Pasteur Institute under the number I 1132, or productive mutants thereof, and an α2-antagonist component which can be obtained by fermentation of the strain *Bacillus licheniformis* SEBR 2464 filed at the CNCM of the Pasteur Institute under the number I-1778, with excipients normally used for formulations of this type, such as those mentioned above.

The form of the compositions according to the present invention may be an emulsion in which the constituent or the mixture of constituents, with an optional stabilizer, is combined with excipients which are commonly used in cosmetic compositions and which are compatible with the said constituents, such as lanolin or plant, mineral or synthetic oils.

The compositions of the invention may also be in the form of a gel in suitable excipients, such as cellulose esters or other gelling agents such as acrylic derivatives and may contain the active principle in dissolved form or suspended as microgranules.

The compositions according to the invention may also take the form of a lotion or a solution in which the mixture of constituents is dissolved or microdispersed.

The form of the compositions according to the invention may thus be a microdispersion in a liquid containing water as well as one or more compatible surfactants. The dispersions have microemulsion properties and have virtually the appearance of true solutions. They may also be prepared at the time of use.

An advantageous form of the compositions according to the invention is a fluid applied topically via an adhesive support, referred to hereinbelow as a "patch", this patch allowing controlled diffusion of the active components, this diffusion possibly being activated by physical phenomena such as electrical microcurrents.

The cosmetic compositions of the present invention may also contain other active components having either an effect of the same type as that of the NPY antagonists, for example products which contribute towards controlling lipolysis/lipogenesis, or collagen synthesis stimulators, collagenase or elastase inhibitors, or vasoprotectors.

The compositions of the present invention are of good stability and may be stored for the time required for use at temperatures of between 0° C. and 60° C. without any sedimentation of the constituents or separation of the phases taking place, and also without their being any decrease in activity which might compromise the use of these compositions.

These compositions are very well tolerated, they have no phototoxicity and their application to the skin for prolonged periods involves no side effects.

The compositions of the present invention, in their various forms of presentation, may be used as lipolysis/lipogenesis regulators in the skin. More particularly, they can be used as cosmetic products for slimming or seborrhoeia-regulating use or as adjuvants in the treatment of acne.

The cosmetic compositions of the present invention may be placed in contact with the epidermis or the hair or pilous system so as to modify the appearance thereof and afford protection thereto.

For example, when these compositions are placed in contact with the epidermis, the latter takes on a "healthy" appearance as if it had been exposed to the air and/or the sun, without, however, tanning, if this is not desired. More particularly, the cosmetic compositions of the present invention make the skin lose its "fatty" appearance with the result of slimming that part of the body with which the said composition is placed in contact and of keeping it in good condition. From the first applications and onwards, the skin relief is smooth and the skin becomes firmer with better tonus. After application for one month, the slimming effect appears, the "orange peel" appearance is visibly attenuated and the figure becomes shaplier.

When the compositions of the present invention are placed in contact with the hair or pilous system, for example after a specific anti-seborrhoeia treatment, the said system is maintained in good condition.

Similarly, the compositions of the present invention keep the facial skin in good condition, also making the formation of comedones more difficult.

A slimming fluid obtained according to Example 12 below was tested on 50 female volunteers who used the said fluid applied twice a day onto the thighs, with very good results.

The slimming fluid described in Example 13 below was tested in a study including 150 female volunteers, carried out under double-blind conditions against placebo. The analysis and comparison of the results obtained with this slimming fluid and with its placebo under the experimental conditions adopted, which are similar to the normal conditions of use for repeated applications over 60 consecutive days on both thighs and the abdomen from the waist to the knees, made it possible to demonstrate a clear and statistically significant slimming effect in favour of the slimming fluid according to the invention relative to the placebo.

The efficacy and tolerance of a slimming fluid as described in Example 14 was tested on more than 1000 women. These tests showed a decrease in the thickness of the adipose tissue, a tonifying and firming action and a slimming effect demonstrated by centimetric echographic measurement and by biphotonic absorptiometry.

One object of the invention is also a cosmetic treatment method, wherein an amount of an NPY antagonist with a cosmetic effect and optionally an amount of an α2-antagonist with a cosmetic effect in a vehicle for cosmetic use is applied to the epidermis and/or the hair or pilous system.

Lastly, the subject of the present invention is the use of an NPY antagonist for the preparation of cosmetic compositions intended to control lipolysis/lipogenesis in the skin, in particular for slimming and seborrhoeia-regulating purposes and as an adjuvant in or after the treatment of acne.

More particularly, the invention relates to the use of an NPY antagonist for the manufacture of cosmetic compositions intended to maintain the facial skin in good condition by making the formation of comedones difficult.

The invention also relates to the use of an NPY antagonist for the manufacture of cosmetic compositions intended for placing in contact with the hair or pilous system. In particular, the invention relates to the use of an NPY antagonist for the manufacture of cosmetic compositions intended to control lipolysis/lipogenesis of the skin, the said compositions also containing an α2-antagonist component.

The examples which follow illustrate the invention without, however, limiting it.

EXAMPLE 1

Preparation of an extract obtained from the strain Streptomyces sp SEBR 2794 (cf. xvI: above)

1.1 Fermentation

The strain Streptomyces sp SEBR 2794 was fermented in six different culture media.

1.1.1.

(a) The strain is propagated in a Petri dish on a subculturing medium:

| | |
|---|---|
| Glucose | 20 g |
| Soyotim (SiO) | 10 g |
| $CaCO_3$ (OMYA) | 3 g |
| Agar type E | 20 g |
| Distilled water qs | 1 l |

The culture is then incubated for 5 days at 28° C. A suspension of spores is then obtained by adding 15 ml of an appropriate mixture having the composition below to each Petri dish:

| | |
|---|---|
| NaCl | 9.00 g |
| KCl | 0.42 g |
| CaCl$_2$ | 0.48 g |
| NaHCO$_3$ | 0.20 g |
| Glycerol | 150.00 g |
| 3-[N-morpholino]propanesulphonic acid (MOPS) | 3.00 g |
| Distilled water qs | 1 l |

(b) 3 ml of this suspension is used to seed 100 ml of culture medium having the following composition:

| | |
|---|---|
| Glucose | 30 g |
| Soyoptim (SIO) | 15 g |
| Tryptone USP (Biokar) | 2 g |
| Yeast extract (Difco) | 5 g |
| Solution of trace elements | 10 ml |
| CaCO$_3$ | 5.00 g |
| Distilled water qs | 1 l |
| pH = 7 | | where the solution of trace elements consists of the following compounds:

| | |
|---|---|
| FeSO$_4$.7H$_2$O | 1.00 g |
| MnSO$_4$.4H$_2$O | 1.00 g |
| CuCl$_2$.2H$_2$O | 0.025 g |
| CaCl$_2$.2H$_2$O | 0.10 g |
| H$_3$BO$_3$ | 0.56 g |
| (NH$_4$)$_6$Mo$_7$O$_{24}$.4H$_2$O | 0.002 g |
| ZnSO$_4$.7H$_2$O | 0.20 g |
| Water qs | 1 l |

The culture is grown at 28° C. for 72 hours in 500 ml conical flasks, stirring at 220 revolutions/minute. The pH at the end of the operation is 7.5.

1.1.2.

(a) A suspension of spores from the strain SEBR 2794 is prepared according to the method indicated in 1.1.1. (a) and (b) 3 ml of this suspension is used to seed 100 ml of culture having the following composition:

| | |
|---|---|
| Glucose | 10 g |
| Soluble starch (Merck) | 30 g |
| Malt extract (Difco) | 5 g |
| Soyoptim (SIO) | 15 g |
| Trypton USP (Biokar) | 2 g |
| Yeast extract (Difco) | 5 g |
| Solution of trace elements (having the same composition as in 1.1.1. (b)) | 10 ml |
| CaCO$_3$ | 5 g |
| Distilled water qs | 1 l |
| pH = 7 | |

The culture is grown as indicated in 1.1.1.

1.1.3. The procedure described in Examples 1.1.1. and 1.1.2. is repeated, changing the composition of the culture medium in step (b), which is as follows:

| | |
|---|---|
| Glycerol (Prolabo) | 10 g |
| Soluble starch (Merck) | 30 g |
| Syoptim (SIO) | 15 g |
| Trypton USP (Biokar) | 2 g |
| Yeast extract (Difco) | 5 g |
| Solution of trace elements (having the same composition as in Example 1) | 10 ml |
| CaCO$_3$ | 5 g |
| Distilled water qs | 1 l |
| pH = 7 | |

The culture is grown as indicated in 1.1.1.

1.1.4.

(a) 0.5 ml of suspension of frozen spores contained in a cryotube of the inoculation batch is used to inoculate a 500 ml flask containing 100 ml of culture medium having the following composition:

| | |
|---|---|
| Yeast extract (Difco) | 3 g |
| Malt extract (Difco) | 3 g |
| Peptone (Difco) | 5 g |
| Glucose | 10 g |
| Distilled water qs | 1 l |

The culture is grown for 72 hours at 28° C., stirring at 220 revolutions/min. The pH of the medium at the end of the operation is close to 7.9.

1.1.5.

(a) The process is carried out according to the method indicated in part (a) of 1.1.4. but three identical cultures are prepared which are stopped at 24 hours old.

(b) The three cultures are combined and are used to inoculate a 20 l fermenter containing 10 l of medium having the following composition:

| | |
|---|---|
| Yeast extract | 3 g |
| Malt extract | 3 g |
| Peptone | 5 g |
| Glucose* | 30 g |
| Distilled water qs | 1 l |

(*): Glucose sterilized separately

The culture is grown for at least 72 hours at 28° C. The aeration is set at 1 VVM (volume of air/volume of culture-minute) and the stirring speed is adjusted so as to maintain a dissolved oxygen pressure of close to 20%. The pH is not regulated and changes freely between 7.2 and 6.3.

1.1.6

(a) The process is performed in the same way as in Example 1.1.5 but using a preculture medium (flasks) having the following composition:

| | |
|---|---|
| Yeast extract (Difco) | 15 g/l |
| Glucose | 10 g/l |
| Distilled water qs | 1 l |

(b) The process is performed in the same way as in Example 1.1.5. but using a culture medium (fermenter) having the following composition:

| | |
|---|---|
| Yeast extract (Difco) | 30 g/l |
| Glucose | 30 g/l |

-continued

| Anti-foaming agent (Struktol) | 1 ml |
| Distilled water qs | 1 ml |

The culture is grown for 144 hours at 28° C.

The aeration is set at 1 VVM (volume of air/volume of culture-minute) and the stirring speed is adjusted so as to maintain a dissolved oxygen pressure of close to 20%. At 72 hours old 10 g/l of glucose are added to prolong the culture. The pH is not controlled and changes freely between 6.5 and 8.

1.2. Extraction 1.2.1. The extraction is carried out on 1.5 liter of broth obtained according to Example 1.1.1.

The fermentation broth is centrifuged at 13,000 revolutions/minute (27,500 g) for 20 minutes and is filtered in the presence of 15 g of filtering adjuvant on a filter press. The filtrate obtained is lyophilized directly and the dry residue thus obtained (16.3 g) is redissolved in 80 ml of water (final pH =8.4).

The 50% inhibitory dilution of this fraction ($ID_{50}$) is $1/4500$.

1.2.2. The extraction is performed on 10 l of culture broth obtained by working according to Example 1.1.5. and are frozen beforehand.

The broth is centrifuged in 500 ml buckets at 8000 rpm (11,000 g) for 20 min. 9 l of completely clear supernatant are obtained.

An aliquot sample is concentrated five times by a Centripep concentrator.

The 50% inhibitory dilution of this fraction is equal to $1/10,000$.

1.2.3. The extraction is performed on 10 l of prefrozen culture broth obtained under the same conditions as in Example 1.1.5.

The separation is performed on a Sharples-type continuous centrifuge.

The 9 l of supernatant obtained are filtered through a 0.2 $\mu$m filter in order to remove all trace of residual biomass.

8.5 l of filtrate are obtained. An aliquot sample is concentrated five times by a Centripep concentrator. The 50% inhibitory dilution of this fraction is $1/16,000$.

1.3. Concentration by ultrafiltration 1.3.1. Concentration on a 5 kD membrane

The process is performed by ultrafiltration of the solution of Example 1.2.1. using an Amicon 5000 membrane in a stirring cell in 25 mM phosphate buffer pH=7.5 containing 150 mM NaCl and an active retentate and a totally inactive permeate are obtained.

1.3.2. Concentration on a 10 kD membrane

A 10 kD Amicon membrane is used to concentrate the 9 liters of supernatant obtained in Example 2.2. By concentrating by a factor of 5, 1.8 l of concentrate five times more active ($ID_{50}=1/10,000$) and a totally inactive permeate are obtained.

1.3.3. Concentration on a 30 kD membrane

A 30 kD Amicon membrane is used to concentrate the 8.5 l of filtrate obtained in Example 2.3. By concentrating by a factor of 5, 1.7 l of concentrate which is up to five times more active ($TD_{50}=1/10,000$) and a permeate containing very weak activity (20% inhibition at $1/250$) are obtained.

1.4. Purification 1.4.1. Gel permeation chromatography

The samples of the solution from 1.2.1. are subjected to gel permeation chromatographies using various gels: Sephadex G 25, G 50, G 75 and G 100 and the results indicated below are obtained:

the activity is eluted at the exclusion volume on Sephadex G 25 and G 50 and very close to the exclusion volume of G 75.

On Sephadex G 100 gel, the activity may be separated from the products of higher molecular weight (>100 KD).

On a Superose 12 analytical column (1 KD to 100 KD fractionation domain), the active molecule showed a retention time of between that of ovalbumin (44 KD) and that of cytochrome (14.4 KD).

1.4.2. Ultrafiltration on a membrane with a cut-off threshold of 5000 daltons 100 ml of a culture supernatant ($ID_{50}=1/3600$) are dialysed in 5 volumes of 20 mM phosphate buffer pH 7.4, 150 mM NaCl, in a magnetically-stirred cell equipped with an Amicon 5000 membrane, and pressurized with compressed air to a pressure of $1\times10^5$ Pa (1 bar).

100 ml of retentate ($ID_{50}$ $1/2500$) freed of molecules of low molecular weight and 500 ml of an ultrafiltrate of negligible activity are recovered.

1.4.3. Ultrafiltration on a membrane with a cut-off threshold of 10,000 daltons 100 ml of a culture supernatant ($ID_{50}$ $1/3600$) are dialysed in 7 volumes of 20 mM phosphate buffer pH 7.4, 150 mM NaCl in a magnetically-stirred cell pressurized to $1\times10^5$ Pa (1 bar) with compressed air and fitted with a Filtron 10K membrane.

100 ml of retentate having an $ID_{50}$ activity=$1/1500$ in terms of inhibition of binding to the NPY receptor are recovered.

The ultrafiltrate (700 ml) is reconcentrated in a cell of the same type fitted with an Amicon 1000 membrane.

100 ml of solution having an $ID_{50}$ value of $1/500$ are obtained.

1.4.4. Removal of the hydrophobic impurities 1500 ml of a culture supernatant are treated for 2 hours, with stirring, with 180 g of polystyrene-divinylbenzene resin (XAD2). The resin is then filtered and washed with twice 300 ml of methanol and then with 300 ml of acetone. The combined methanol and acetone solutions are evaporated under vacuum. The residue taken up in 40 ml of methanol gives a solution which has no activity.

The aqueous solution freed of the hydrophobic products is lyophilized.

The residue taken up in 80 ml of water gives a solution having an $ID_{50}$ value of 1/4500 in terms of inhibition of binding to the NPY receptor.

1.4.5. Extraction of the active molecule by cation exchange.

1500 ml of a culture supernatant are adjusted to pH 5 with 1 N acetic acid and are then treated with 120 g of cation exchange resin (Dowex 50 WX-4, ACO form).

After stirring for one hour, the resin is filtered and then desorbed with 300 ml of 1N aqueous ammonia for half an hour. This solution is then lyophilized. The residue obtained taken up in 40 ml of water gives a solution which, when measured in terms of inhibition of binding to the NPY receptor, has an $ID_{50}$ value of 1/3600.

Solutions with NPY receptor antagonist activity may also be obtained by extracting the culture broths of Examples 1.1.2, 1.1.3, 1.1.4 and 1.1.6 according to the extraction examples described in 1.2.1 to 1.2.3.

EXAMPLE 2

Preparation of an extract obtained from the strain *Bacillus licheniformis* SEBR 2464 (cf. XXVII above)

2.1 Fermentation

The strain *Bacillus licheniformis* SEBR 2464 was fermented in 4 different culture media.

2.1.1.

(a) The strain is propagated in Petri dishes on a subculturing medium having the following composition:

| Bacto tryptic Soy Broth (Difco) | 40 g |
|---|---|
| MOPS | 2 g |
| Yeast extract (Difco) | 5 g |
| Agar type E | 20 g |
| Distilled water qs | 1 l |

The culture is incubated for 48 hours at 30° C. A suspension of spores is then obtained by adding 15 ml of a suitable maintenance medium having the composition below to each Petri dish:

| NaCl | 9.00 g |
|---|---|
| KCl | 0.42 g |
| CaCl$_2$ | 0.48 g |
| NaHCO$_3$ | 0.20 g |
| Glycerol | 150.00 g |
| MOPS | 3.00 g |
| Distilled water qs | 1 l |

(b) 3 ml of this suspension are used to seed 200 ml of culture medium having the following composition:

| Tryptone USP (Difco) | 30 g |
|---|---|
| Papain peptone from soya (Difco) | 5 g |
| NaCl | 5 g |
| Distilled water qs | 1 l |
| pH = 7 | |

The culture is grown at 30° C. for 24 hours in 500 ml conical flasks, stirring at 260 revolutions/minute.

2.1.2. 1.5 ml of frozen suspension of spores of the secondary inoculation batch are used to inoculate a 500 ml flask containing 100 ml of culture medium having the following composition:

| Glucose | 30 g* |
|---|---|
| Yeast extract (Difco) | 10 g |
| MgSO$_4$.7H$_2$O | 0.5 g |
| KH$_2$PO$_4$ | 1 g |
| Solution of trace elements | 100 ml |
| Distilled water qs | 1 l |

*Glucose sterilized separately where the solution of trace elements consists of the following compounds:

| FeSO$_4$.7H$_2$O | 1.00 g |
|---|---|
| MnSO$_4$.4H$_2$O | 1.00 g |
| CuCl$_2$.2H$_2$O | 0.025 g |
| CaCl$_2$.2H$_2$O | 0.10 g |
| H$_3$BO$_3$ | 0.56 g |
| (NH$_4$)$_6$Mo$_7$O$_{24}$.4H$_2$O | 0.02 g |
| ZnSO$_4$.7H$_2$O | 0.20 g |
| Distilled water qs | 1 l |

The culture is grown at 30° C. with stirring at 260 rpm. The culturing is stopped at 15 hours old.

2.1.3. 300 ml of culture in stirred flasks are prepared in the same way as in Example 2.1.2. and this culture is used to inoculate a 20 l fermenter containing 10 l of medium of the same composition, to which is added 1 ml/l of strucktol. The culture is grown for 15 hours at 30° C. with stirring at 260 rpm and an aeration of 0.5 VVM.

2.1.4.
(a) 5 cultures in 1 l stirred flasks containing 300 ml of medium having the composition below are prepared:

| Glucose | 30 g |
|---|---|
| Yeast extract (Difco) | 30 g |
| MgSO$_4$.7H$_2$O | 0.5 g |
| KH$_2$PO$_4$ | 1 g |
| Solution of trace elements | 10 ml |
| Distilled water qs | 1 l |

The solution of trace elements has the same composition as in Example 2.1.2.

(b) The 5 cultures are grown for 15 hours at 30° C. and at 220 rpm and are then combined to inoculate a 75 l fermenter containing 50 l of medium having the following composition:

| Glucose | 30 g |
|---|---|
| Yeast extract (Difco) | 30 g |
| MgSO$_4$.7H$_2$O | 1 g |
| KH$_2$PO$_4$ | 2 g |
| Solution of trace elements | 20 ml |
| Strucktol | 2 ml |
| Distilled water qs | 1 l |

The solution of trace elements has the same composition as in Example 1.1.1.

The culture is grown at 30° C. with an aeration of 0.5 VVM and stirring adjusted so as to maintain a dissolved oxygen pressure of close to 20%. At 7 hours old a concentrated glucose solution is added to prolong the growth. The culturing is stopped at the growth plateau at 16 hours old.

2.2. Extraction 2.2.1. The extraction is performed on 12 l of culture broth of 2.1.1.

The broth is centrifuged at 13,000 revolutions/minute (27,500 g) for 10 min and 11 l of supernatant are obtained. 2.1 kg of Amberlite XAD2 resin preconditioned with methanol and acetone are added to these 11 l of supernatant.

The supernatant/resin mixture is placed together overnight at room temperature.

The resin is then filtered off and the products bound thereto are successively eluted with twice 5 liters of methanol and with 5 liters of acetone.

The organic phases are combined after filtration and evaporated to dryness under vacuum.

The evaporation residue (46 g) constitutes the dry extract; it is redissolved in 100 ml of propylene glycol/water mixture (50/50).

The fraction thus obtained has an ID50 value=$1/3000$.

2.2.2. The extraction is performed on 3.5 l of culture broth of Example 2.1.3.

The same procedure as in Example 2.2.1. is followed but the amounts of resin and of solvent are adapted to the volume of supernatant treated.

11 g of dry extract are obtained, which are taken up in 27 ml of the propylene glycol/water mixture (50/50).

The solution thus obtained has an ID$_{50}$ value $1/4000$.

2.2.3. The extraction is performed on 50 l of culture broth of Example 2.1.4.

A tangential microfiltration system (0.2 μm) is used to separate the biomass. 46 l of permeate are obtained, which are placed in contact with 9 kg of preconditioned Amberlite XAD$_2$ resin overnight at room temperature.

The loaded resin is then filtered off and the products bound thereto are eluted with twice 23 l of methanol and once 23 l of acetone. Between each elution, the organic phase and the resin are separated by filtration.

The organic phases are then combined and evaporated to dryness under vacuum.

285 g of dry extract are obtained, which are taken up with 620 g of the propylene glycol/water mixture (50/50).

The solution obtained is filtered through a 0.2 μm filter and has an $ID_{50}$ value=⅛₂₀₀.

A solution with α2-receptor antagonist activity may also be obtained by extracting the culture broth of Example 2.1.2. according to Example 2.2.3.

EXAMPLE 3

The following composition is prepared for application to the skin in the form of a slimming gel:

| | |
|---|---|
| Carbopol 940 | 0.20 g |
| Polyethylene glycol | 3.00 g |
| Preserving agents | 0.75 g |
| Tween 20 | 0.50 g |
| Triethanolamine | 0.25 g |
| Escin | 0.50 g |
| Caffeine | 0.50 g |
| Extract of *Centella asiatica* | 3.00 g |
| Extract of *Ginkgo biloba* | 3.00 g |
| Carnitine | 4.00 g |
| Extract of Example 2.2.1. | 0.10 g |
| Dry extract of Example 1.2.1. | 0.01 g |
| Demineralized water qs | 100.00 g |

EXAMPLE 4

The following composition, which can be used for application to the skin as a slimming emulsion, is prepared:

| | |
|---|---|
| Carbopol 934 | 0.300 g |
| Triethanolamine | 0.520 g |
| Escin | 0.500 g |
| Cetyl alcohol | 1,500 g |
| Fluid fatty esters | 8.500 g |
| Cetyl palmitate | 2.000 g |
| Phytosterol | 1.000 g |
| POE cetyl alcohol | 0.700 g |
| Silicone oil | 2.500 g |
| Polysorbate 60 | 1.900 g |
| Sorbitan stearate | 1.400 g |
| Propylene glycol | 4.000 g |
| Preserving agents | 0.700 g |
| Extract of spleen | 1.000 g |
| Carnitine | 4.000 g |
| Extract of Example 2.2.1. | 0.0015 g |
| Dry extract of Exmaple 1.3.1. | 0.0010 g |
| Demineralized water qs | 100.00 g |

EXAMPLE 5

The following composition, which can be used for application to the skin in the form of a slimming microemulsion, is prepared:

| | |
|---|---|
| Caffeine | 0.50 g |
| Escin | 0.50 g |
| Ethyoxylated triglycerides | 25.70 g |
| Extract of spleen | 1.00 g |
| Carnitine | 4.00 g |

-continued

| | |
|---|---|
| Ethoxylated fatty alcohols | 12.00 g |
| Synthetic triglycerides | 7.00 g |
| Silicone oil | 3.50 g |
| Fatty ester | 3.50 g |
| Preserving agents | 0.75 g |
| Dry extract of Example 1.4.3. | 0.004 g |
| Extract of Example 2.2.1. | 0.15 g |
| Demineralized water qs | 100.00 g |

EXAMPLE 6

The following composition for application to the skin in the form of a slimming microemulsion is prepared:

| | |
|---|---|
| Caffeine | 1.00 g |
| Escin | 0.50 g |
| Ethyoxylated triglycerides | 25.70 g |
| Extract of spleen | 1.00 g |
| Carnitine | 2.00 g |
| Ethoxylated fatty alcohols | 12.00 g |
| Synthetic triglycerides | 8.00 g |
| Silicone oil | 3.50 g |
| Fatty ester | 3.50 g |
| Preserving agents | 0.75 g |
| Dry extract of Example 1.4.3. | 0.001 g |
| Demineralized water qs | 100.00 g |

EXAMPLE 7

| | |
|---|---|
| Carbopol 940 | 0.20 g |
| Polyethylene glycol | 3.00 g |
| Preserving agents | 0.75 g |
| Tween 20 | 0.50 g |
| Triethanolamine | 0.25 g |
| Carnitine | 4.00 g |
| Dry extract of Example 1.2.1 | 0.10 g |
| Demineralized water qs | 100.00 g |

EXAMPLE 8

Slimming patch

| | |
|---|---|
| Adhesive | qs 100 |
| Extract of Example 1.3.2. | 0.020 |
| Extract of Example 2.2.3. | 0.001 |

*The adhesive may be polyisobutene, an acrylic or silicone adhesive or any other biocampatible adhesive.

EXAMPLE 9

Alcoholic gel

| | |
|---|---|
| Alcohol | 10.00 g |
| Carbomer | 0.20 g |
| Glycereth-26 | 5.00 g |
| Sodium hydroxide | 0.08 g |
| Propyl cellulose | 0.10 g |
| Extract of Example 1.3.2. | 0.02 g |
| Demineralized water qs | 100.00 g |

EXAMPLE 10
Alcoholic gel

| | |
|---|---|
| Alcohol | 40.00 g |
| Carbomer | 0.50 g |
| Glycereth-26 | 5.00 g |
| Sodium hydroxide | 0.20 g |
| Propyl cellulose | 0.10 g |
| Extract of Example 1.3.2. | 0.20 g |
| Demineralized water qs | 100.00 g |

EXAMPLE 11
Slimming gel/cream

| | |
|---|---|
| Glyceryl stearate | 5.00 g |
| Cetyl alcohol | 1.50 g |
| Caprylic/capric succinate | 6.00 g |
| Silicone oil | 2.00 g |
| Parabens | 0.30 g |
| Xanthan gum | 0.40 g |
| Butylene glycol | 5.00 g |
| Phenoxetol | 0.70 g |
| Polyglyceryl methacrylate | 3.00 g |
| Extract of Example 1.3.2. | 0.02 g |
| Demineralized water qs | 100.00 g |

EXAMPLE 12
Slimming macroemulsion

| | |
|---|---|
| Glycerol | 10.000 |
| Mineral oil | 6.000 |
| Panthenol | 1.000 |
| Copolymer acrylates | 0.500 |
| Triethanolamine | 0.500 |
| Parabens | 0.300 |
| Phenoxyethanol | 0.700 |
| Extract of Example 1.3.2. | 0.020 |
| Demineralized water qs | 100.00 g | hexane dihydrochloride, class A, group VI (Example 21);
BIBP 3226, class A, group VII (Example 22);
He 90481, class A, group VIII (Example 23);
dimethyl 1,4-dihydro-4-[3-[[[(3-[spiro(indene-4,1'-piperid-1-yl)]propyl]amino]carbonyl]amino]phenyl]-2,6-dimethyl-3,5-pyridinedicarboxylate, class A, group IX (Example 24).

What is claimed is:

1. A slimming composition for topical application comprising a neuropeptide Y antagonist and an α2 antagonist in combination with cosmetically acceptable excipient, wherein the neuropeptide Y antagonist is a fermentation product of the strain Streptomyces sp SEBR 2794 as well as productive mutants thereof.

2. A slimming composition according to claim 1 comprising about 0.00001 % to 5% of neuropeptide Y antagonist and about 0.00001 % to 5% of α2 antagonist.

3. A slimming composition for topical application comprising a neuropeptide Y antagonist and an a2 antagonist in combination with cosmetically acceptable excipient, wherein the a2 antagonist is a fermentation product of the strain *Bacillus licheniformis* SEBR 2464 as well as productive mutants thereof.

4. A slimming composition according to claim 3 comprising about 0.00001 % to 5% of neuropeptide Y antagonist and about 0,00001%Y to 6% of a2 antagonist.

5. A slimming composition for topical application comprising a neuropeptide Y antagonist and an α2 antagonist in combination with cosmetically acceptable excipient, wherein the neuropeptide Y antagonist is a fermentation product of the strain Streptomyces sp SEBR 2794 and the a2 antagonist is a fermentation product of the strain *Bacillus licheniformis* SEBR 2464.

6. A slimming composition according to claim 5 comprising about 0.00001% to 5% of neuropeptide Y antagonist and about 0.00001 % to 15% of α2 antagonist.

7. A slimming composition for topical application comprising a neuropeptide Y antagonist and an α2 antagonist in combination with cosmetically acceptable excipient, additionally containing caffeine and extract of Ginkgo biloba.

8. A slimming composition according to claim 7 comprising about 0,00001 % to 5% of neuropeptide Y antagonist and about 0.00001% to 5% of α2 antagonist.

9. A slimming composition for topical application comprising a neuropeptide Y antagonist and an α2 antagonist in combination with cosmetically acceptable excipient, additionally containing a collagen synthesis stimulator, a collagenase or elastase inhibitor, or a vasoprotector.

10. A method of achieving a slimming effect, which process comprises topically applying to selected parts of the body a slimming composition for topical application comprising a neuropeptide Y antagonist and an α2 antagonist in combination with cosmetically acceptable excipient.

11. A method according to claim 10 comprising about 0.00001% to 5% of neuropeptide Y antagonist and about 0.00001% to 5% of α2 antagonist.

12. A method according to claim mming effect, which process comprises topically applying a slimming composition according to claim 5 to selected parts of the body.

13. A method according to claim 10, wherein the slimming composition is applied to the thighs.

14. A method according to claim 10, wherein the slimming composition is applied to the thighs and the abdomen from the waist to the knees.

15. A method of controlling lipolysis/lipogenesis in the skin which comprises applying to the skin a slimming composition for topical application comprising a neuropeptide Y antagonist and an α2 antagonist in combination with cosmetically acceptable excipient.

16. A method of attenuating the fatty, "orange peel" appearance of the skin which comprises applying to the skin a A slimming composition for topical application comprising a neuropeptide Y antagonist and an α2 antagonist in combination with cosmetically acceptable excipient.

* * * * *

UNITED STATES PATENT AND TRADEMARK OFFICE
CERTIFICATE OF CORRECTION

PATENT NO. : 6,114,336
DATED : September 5, 2000
INVENTOR(S) : Elisabeth Blanc-Ferras et al.

It is certified that error appears in the above-identified patent and that said Letters Patent is hereby corrected as shown below:

Column 37,
After example 12.

EXAMPLE 13
Slimming macroemulsion

| Glycerol | 5.000 |
|---|---|
| Mineral oil | 2.00 |
| Panthenol | 0.500 |
| Copolymer acrylates | 0.050 |
| Triethanolamine | 0.050 |
| Parabens | 0.300 |
| Phenoxyethanol | 0.700 |
| Extract of Example 1.3.2. | 0.020 |
| Extract of Example 2.2.3 | 0.001 |
| Demineralized water qs | 100.00 g |

EXAMPLES 14 to 25

A slimming microemulsion having the composition of Example 6 above is prepared, in which the dry extract of Example 1.4.3. is replaced by:

- 1-(2-[[N-(2-naphthylsulphamoyl)-5-methoxy-2-indol-yl)carboxamido]-3-(4-[N-(4-(dimethylaminomethyl)-trans-cyclohexylmethyl]amidino)phenyl)propionyl]pyrrolidine, class A, group I (Example 14);
- 3-(4-methoxyphenyl)-4-[4-(2-pyrrolidin-1-ylethoxy)-benzoyl]-1,2-dihydronaphthalene hydrochloride, class A, group IIa (Example 15);
- 2-(4-hydroxyphenyl)-3-[4-(2-pyrrolidin-1-ylethoxy)-benzoyl]benzothiophene hydrochloride, class A, group IIb (Example 16);
- PD 160170, class A, group III (Example 17);
- SC 3117, class A, group IV (Example 18);
- D-myoinositol 1,2,6-triphosphate, class A, group Va (Example 19);
- inositol monophosphate, zinc salt, class A, group Vb (Example 20);
- 1-(3-methoxyphenyl)-1-(4-phenylpiperazin-1-yl)cyclo- Signed and Sealed this Twelfth Day of February, 2002

Attest:

*Attesting Officer*

JAMES E. ROGAN
*Director of the United States Patent and Trademark Office*